United States Patent
Sexton et al.

(10) Patent No.: US 11,815,516 B2
(45) Date of Patent: Nov. 14, 2023

(54) PROTEIN BIOMARKERS FOR DISEASES ASSOCIATED WITH THE CONTACT ACTIVATION SYSTEM

(71) Applicant: Takeda Pharmaceutical Company Limited, Osaka (JP)

(72) Inventors: Daniel J. Sexton, Melrose, MA (US); Malini Viswanathan, Acton, MA (US); Ryan Faucette, Melrose, MA (US); Tripti Gaur, South Grafton, MA (US)

(73) Assignee: Takeda Pharmaceutical Company Limited, Osaka (JP)

(*) Notice: Subject to any disclaimer, the term of this patent is extended or adjusted under 35 U.S.C. 154(b) by 922 days.

(21) Appl. No.: 16/333,155

(22) PCT Filed: Sep. 15, 2017

(86) PCT No.: PCT/US2017/051749
§ 371 (c)(1),
(2) Date: Mar. 13, 2019

(87) PCT Pub. No.: WO2018/053244
PCT Pub. Date: Mar. 22, 2018

(65) Prior Publication Data
US 2021/0285962 A1 Sep. 16, 2021

Related U.S. Application Data

(60) Provisional application No. 62/518,492, filed on Jun. 12, 2017, provisional application No. 62/395,712, filed on Sep. 16, 2016.

(51) Int. Cl.
*G01N 33/00* (2006.01)
*A61K 39/00* (2006.01)
*G01N 33/68* (2006.01)
*A61K 38/08* (2019.01)
*C07K 16/40* (2006.01)

(52) U.S. Cl.
CPC ......... *G01N 33/6893* (2013.01); *A61K 38/08* (2013.01); *C07K 16/40* (2013.01); *G01N 2333/47* (2013.01); *G01N 2333/90* (2013.01); *G01N 2333/99* (2013.01); *G01N 2800/22* (2013.01); *G01N 2800/52* (2013.01)

(58) Field of Classification Search
CPC ........... G01N 33/6893; G01N 2333/47; G01N 2333/90; G01N 2333/99; G01N 2800/22; G01N 2800/52; A61K 38/08; C07K 16/40
See application file for complete search history.

(56) References Cited

U.S. PATENT DOCUMENTS

| | | |
|---|---|---|
| 2004/0009491 A1 | 1/2004 | Birse et al. |
| 2006/0029594 A1 | 2/2006 | Ames et al. |
| 2007/0192882 A1 | 8/2007 | Dewald |
| 2008/0280811 A1 | 11/2008 | Feener et al. |
| 2009/0064350 A1 | 3/2009 | Dewald |
| 2009/0104605 A1 | 4/2009 | Siuzdak et al. |
| 2012/0082676 A1 | 4/2012 | Ghebrehiwet |

FOREIGN PATENT DOCUMENTS

| | | |
|---|---|---|
| CN | 105073778 A | 11/2015 |
| CN | 105377894 A | 3/2016 |
| CN | 105452860 A | 3/2016 |
| CN | 105874332 A | 8/2016 |
| JP | 2001-174463 A | 6/2001 |
| JP | 2012-501184 A | 1/2012 |
| JP | 2016-511823 A | 4/2016 |
| KR | 1020110090842 A | 8/2011 |
| WO | WO 2010/025369 A2 | 3/2010 |
| WO | WO 2015/061183 A1 | 4/2015 |
| WO | WO2015061183 * | 4/2015 |
| WO | WO 2015/112578 A1 | 7/2015 |
| WO | WO 2015/158765 A1 | 10/2015 |
| WO | WO 2018/053247 A1 | 3/2018 |
| WO | WO 2018/053260 A1 | 3/2018 |

OTHER PUBLICATIONS

Farkas et al, Clinic Rev Allerg Immunol 51: 140-151, May 2016, IDS filed on May 31, 2019, NPL, item 3 (Year: 2016).*
Coelho et al, Frontiers in Immunology 2:1-7, published Jan. 2012 (Year: 2012).*
Bork, Diagnosis and treatment of hereditary angioedema with normal C1 inhibitor. Allergy Asthma Clin Immunol. Jul. 28, 2010;6(1):15. doi: 10.1186/1710-1492-6-15.
Cugno et al., Plasma biomarkers of acute attacks in patients with angioedema due to C1-inhibitor deficiency. Allergy. Feb. 2009;64(2):254-7. doi: 10.1111/j.1398-9995.2008.01859.x. Epub Dec. 4, 2008.
Farkas et al., "Nuts and Bolts" of Laboratory Evaluation of Angioedema. Clin Rev Allergy Immunol. Oct. 2016;51(2):140-51. doi: 10.1007/s12016-016-8539-6.
Craig et al., Diagnosis and treatment of bradykinin-mediated angioedema: outcomes from an angioedema expert consensus meeting. Int Arch Allergy Immunol. 2014;165(2):119-27. doi: 10.1159/000368404. Epub Nov. 15, 2014.
Csuka et al., Activation of the ficolin-lectin pathway during attacks of hereditary angioedema. J Allergy Clin Immunol. Dec. 2014;134(6):1388-1393.e1. doi: 10.1016/j.jaci.2014.05.030. Epub Jul. 16, 2014.
Czúcz et al., Endothelial cell function in patients with hereditary angioedema: elevated soluble E-selectin level during inter-attack periods. J Clin Immunol. Feb. 2012;32(1):61-9. doi: 10.1007/s10875-011-9606-7. Epub Oct. 19, 2011.

(Continued)

*Primary Examiner* — Lei Yao
(74) *Attorney, Agent, or Firm* — Wolf, Greenfield & Sacks, P.C.

(57) ABSTRACT

Provided herein are methods and kits for analyzing a biological sample obtained from a subject having, suspected of having, or being at risk for a disease associated with the contact activation system.

18 Claims, 9 Drawing Sheets

Specification includes a Sequence Listing.

(56) References Cited

OTHER PUBLICATIONS

Nov. 30, 2017, Invitation to Pay Additional Fees.
Jan. 23, 2018, International Search Report and Written Opinion.
Mar. 28, 2019, International Preliminary Report on Patentability.
Cui et al., Advances in the Pathogenesis of Hereditary Angioedema. Shaanxi Medical Journal. Oct. 5, 2007;36(10):1402-3.
Dai et al., Role of Bradykinin in the Pathogenesis of Allergic Diseases. Chin J Allergy Clin Immunol. Dec. 30, 2014;8(4):306-11.
Kelemen et al., Baseline level of functional C1-inhibitor correlates with disease severity scores in hereditary angioedema. Clin Immunol. Mar. 2010;134(3):354-8. doi: 10.1016/j.clim.2009.11.002. Epub Nov. 27, 2009.
Liu et al., Revision of the Biological Significance of the Contact System. Advances in Physiological Sciences. Jan. 30, 2000;31(1):7-12.
Peng et al., Advance in interleukin-36 and its role in inflammatory diseases. Chin J Pharmacol Toxicol. Apr. 15, 2015;29(2):317-22.
Riedl M.A., Hereditary angioedema with normal C1-INH (HAE type III). J Allergy Clin Immunol Pract. Sep.-Oct.2013;1(5):427-32. doi: 10.1016/j.jaip.2013.06.004. Epub Aug. 2, 2013.
Veszeli et al., Neutrophil activation during attacks in patients with hereditary angioedema due to C1-inhibitor deficiency. Orphanet J Rare Dis. Dec. 10, 2015;10:156(1-8). doi: 10.1186/s13023-015-0374-y.
Zhao et al., Hereditary Angioedema. J Clin Pediatr. Mar. 15, 2010;28(3):297-99.
Ohsawa et al., Clinical and laboratory characteristics that differentiate hereditary angioedema in 72 patients with angioedema. Allergol Int. Dec. 2014;63(4):595-602. doi: 10.2332/allergolint.14-OA-0700.
Wilcox S.K., The SOMAscan® assay and SOMAmer® reagents: Translatable tools from high-throughput biomarker discovery to targeted assays. eSeminar. Aug. 18, 2016, https://www.agilent.com/cs/library/eseminars/public/SomaLogic_Agilent_081816.pdf [last accessed Dec. 27, 2022]. 33 pages.

* cited by examiner

A

B

A

B

A

ATPO

B

Cyclophilin F

FIGURE 4, CONTINUED
C
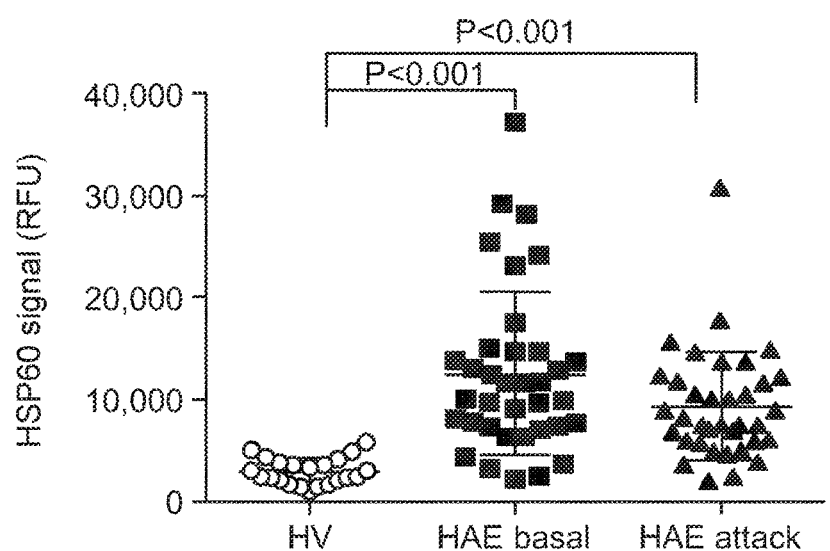

14-3-3 protein zeta/delta

IL-1F6

FIGURE 7, CONTINUED
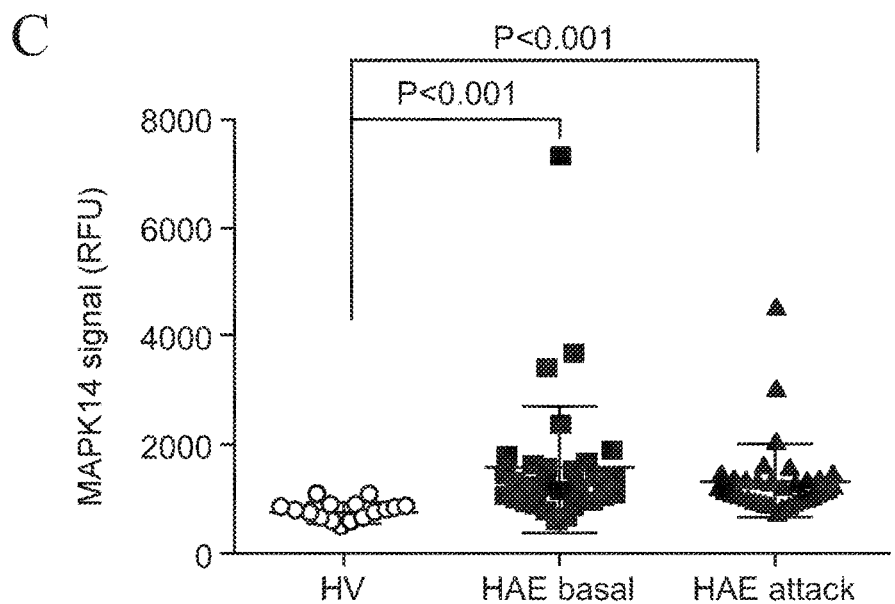
FIGURE 8
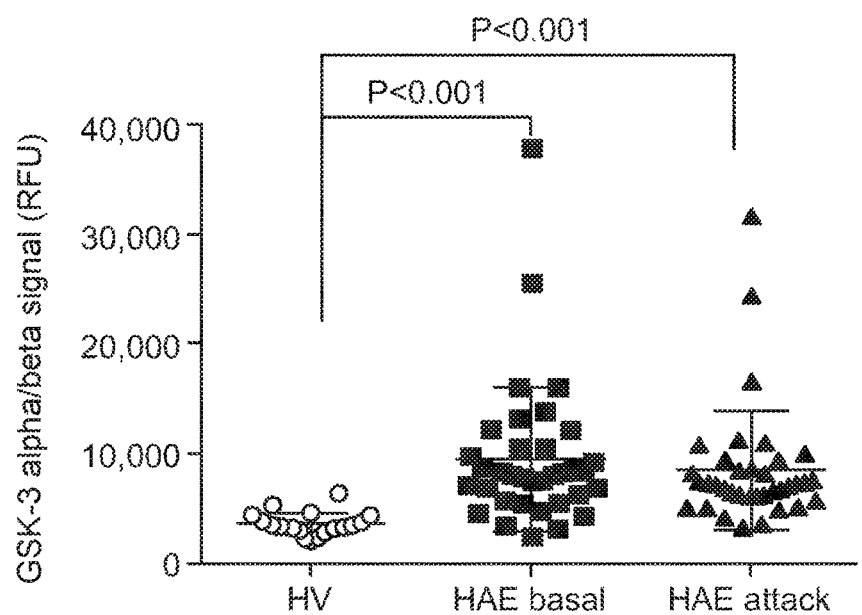

```
                         SEQUENCE LISTING

<160> NUMBER OF SEQ ID NOS: 5

<210> SEQ ID NO 1
<211> LENGTH: 304
<212> TYPE: PRT
<213> ORGANISM: Homo sapiens

<400> SEQUENCE: 1

Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala Asp Ser Glu Glu
            20                  25                  30

Asp Glu Glu His Thr Ile Ile Thr Asp Thr Glu Leu Pro Pro Leu Lys
        35                  40                  45

Leu Met His Ser Phe Cys Ala Phe Lys Ala Asp Asp Gly Pro Cys Lys
    50                  55                  60

Ala Ile Met Lys Arg Phe Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
    130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270
```

```
Gln Arg Ile Ser Lys Gly Gly Leu Ile Lys Thr Lys Arg Lys
            275                 280                 285

Lys Gln Arg Val Lys Ile Ala Tyr Glu Glu Ile Phe Val Lys Asn Met
290                 295                 300

<210> SEQ ID NO 2
<211> LENGTH: 58
<212> TYPE: PRT
<213> ORGANISM: Homo sapiens

<400> SEQUENCE: 2

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 3
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 3

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60

<210> SEQ ID NO 4
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Ile Met Met Trp Val Arg Gln Ala Pro Gly Lys Gly Leu Glu Trp Val
        35                  40                  45

Ser Gly Ile Tyr Ser Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Arg Arg Ile Gly Val Pro Arg Arg Asp Glu Phe Asp Ile Trp
            100                 105                 110
```

```
Gly Gln Gly Thr Met Val Thr Val Ser Ser
        115                 120

<210> SEQ ID NO 5
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 5

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Trp Thr
                85                  90                  95

Phe Gly Gln Gly Thr Lys Val Glu Ile
            100                 105
```

PROTEIN BIOMARKERS FOR DISEASES ASSOCIATED WITH THE CONTACT ACTIVATION SYSTEM

CROSS REFERENCE TO RELATED APPLICATIONS

This application is a national stage filing under 35 U.S.C. § 371 of international application number PCT/US2017/051749, filed Sep. 15, 2017, which claims the benefit under 35 U.S.C. § 119(e) of U.S. provisional application No. 62/518,492, filed Jun. 12, 2017 and U.S. provisional application No. 62/395,712, filed Sep. 16, 2016. The entire contents of each of these referenced applications are incorporated by reference herein.

BACKGROUND

The plasma contact activation system is a pro-inflammatory and pro-coagulant system involving a group of plasma proteases. It is activated by either factor XIIa upon exposure to foreign or negatively charged surfaces or on endothelial cell surfaces by prolylcarboxypeptidases (Sainz I. M. et al., Thromb. Haemost. (2007) 98, 77-83). Inappropriate or unregulated activation of the contact system has been implicated in various diseases, including hereditary angioedema (HAE).

HAE is a disease that causes episodic attacks of swelling, which can affect multiple parts of the body such as the face, extremities, genitals, GI tract and upper airways. Because HAE symptoms often resemble symptoms of allergies or intestinal colics, HAE patients are often difficult to identify until they exhibit severe or life-threatening symptoms. Early diagnosis would allow for better management of emergency situations involving acute HAE attacks and would also help manage HAE patients to prevent or dampen acute HAE episodes, e.g., allowing an HAE sufferer to avoid exposure to stimuli that might trigger HAE episodes.

It is therefore of great interest to identify biomarkers for HAE and develop reliable diagnostic and prognostic methods for identifying subjects having certain types of HAE or being at risk of suffering an acute HAE attack. Such biomarkers would also benefit the studies on disease mechanisms, which could facilitate the development of effective new therapies for the disease.

SUMMARY OF THE PRESENT DISCLOSURE

The present disclosure is based on the identification of proteins that are differentially present in biological samples obtained from subjects having diseases associated with the contact activation system as compared to healthy individuals or differentially present in biological samples obtained from subjects in different stages of such a disease (e.g., attack versus quiescence).

Accordingly, one aspect of the present disclosure provides methods of analyzing a sample comprising (i) providing a biological sample (e.g., serum sample or a plasma sample) obtained from a subject, such as a human subject, having, suspected of having, or being at risk for a disease associated with the contact activation system; and (ii) measuring the level of a biomarker set, which comprises at least one protein selected from Table 1, wherein if the biomarker set consists of one protein, said protein is not C4, plasma prekallikrein, thrombin, tissue-type plasminogen activator (tPA), and heat shock protein 90. In some embodiments, the disease associated with the contact activation system is hereditary angioedema (HAE), such as type 1 HAE or type II HAE.

In some embodiments, the biomarker set consists of 2-10 proteins selected from Table 1. In some embodiments, the at least one protein is a mitochondrial protein, which can be ATP synthase subunit O (ATPO), cyclophilin F, or mitochondrial heat shock protein 60 (HSP60). In some embodiments, the at least one protein is 14-3-3 zeta/delta or 14-3-3 beta/alpha. In some embodiments, the at least one protein is a protein kinase, which can be protein kinase YES, protein kinase LYN, or mitogen-activated protein kinase 14 (MAPK14). In some embodiments, the at least one protein is glycogen synthase kinase 3 alpha/beta. In some embodiments, the at least one protein is ATP-dependent RNA helicase DDX19B (DEAD box 19B). In some embodiments, the at least one protein is eukaryotic translation initiation factor 5A-1 (eIF-5A-1).

In some embodiments, providing a biological sample comprises collecting the biological sample into an evacuated blood collection tube, which comprises one or more protease inhibitors. In some embodiments, the measuring the level of a biomarker set is performed using an enzyme-linked immunosorbent assay (ELISA), an immunoblotting assay, or a lateral flow assay.

In some embodiments, the method further comprises identifying the subject as having a disease associated with the contact system, if the level of the biomarker set of the subject deviates from the level of the same biomarker set of a control subject. In some embodiments, the method further comprises administering to the subject an effective amount of a therapeutic agent for treating the disease, such as a plasma kallikrein (pKal) inhibitor, a bradykinin 2 receptor inhibitor, and/or a C1 esterase inhibitor, if the subject is identified as having the disease. In some embodiments the pKal inhibitor is an anti-pKal antibody (e.g., lanadelumab) or an inhibitory peptide (e.g., ecallantide). In some examples, the bradykinin 2 receptor inhibitor is an inhibitory peptide (e.g., icatibant). In some examples, the C1 esterase inhibitor is a human plasma-derived C1 esterase inhibitor.

In some embodiments, the subject is a human patient who is on a treatment for the disease, and wherein the method further comprises assessing the efficacy of the treatment based on the level of the biomarker set, a deviation of the level of the biomarker set of the subject from that of a control subject being indicative of the treatment efficacy. In some embodiments, the method further comprises identifying a suitable treatment for the subject based on the level of the biomarker set. In some embodiments, the method further comprises identifying the subject as a candidate for a treatment of the disease based on the level of the biomarker set.

The present disclosure provides biomarkers capable of identifying patients with diseases associated with the contact activation system (e.g., HAE). Measuring the levels of the biomarker sets may also be useful in the evaluation and treatment of such diseases.

In another aspect, a kit is provided for analyzing a sample of a subject having, suspected of having, or at risk for a disease associated with the contact system, the kit comprising a first binding agent specific to a first protein biomarker selected from Table 1; and a second binding agent specific to a second protein biomarker selected from Table 1; wherein the first protein biomarker and the second protein biomarker are different. In some examples, the first and/or the second binding agent is an antibody specific to the protein marker. In some embodiments, the kit may further comprise a first detection agent that binds to the first binding agent and a second detection agent that binds to the second binding agent. In some embodiments, the first binding agent and the second binding agent are immobilized on a support member.

The details of one or more embodiments of the present disclosure are set forth in the description below. Other features or advantages of the present disclosure will be apparent from the following drawings and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIG. 8 presents a graph showing glycogen synthase kinase 3 alpha/beta (GSK-3 alpha/beta) protein levels in plasma samples from patients having HAE (type I/type II) at basal level ("HAE basal"), from HAE patients during an HAE attack ("HAE attack) and from healthy individuals ("HV"). RFU is relative fluorescence units.

DETAILED DESCRIPTION

Figure 1:
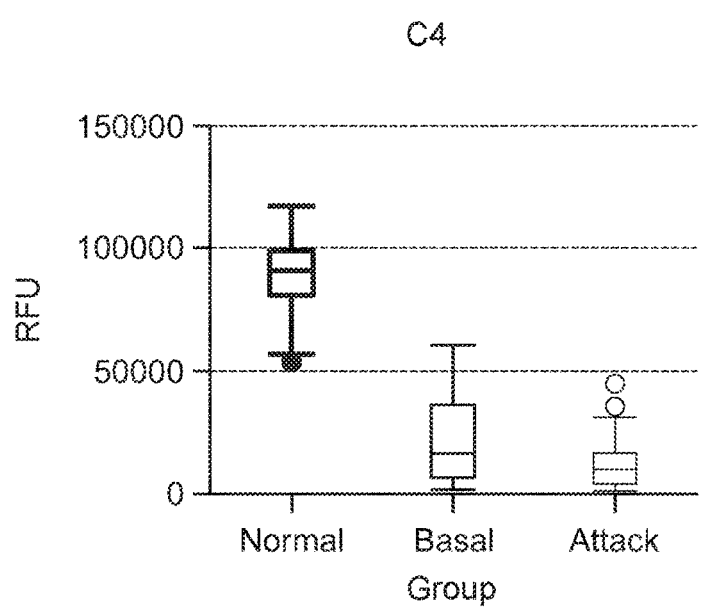
FIG. 1 presents box plots showing protein levels detected in plasma samples from patients having HAE (type I/type II) at basal level ("Basal," N=33) and during an HAE attack ("Attack," N=33) and healthy individuals ("Normal," N=22). A: complement protein 4 (C4) levels. B: prekallikrein levels in plasma samples obtained from healthy individuals (N=22), basal HAE (I/II) (N=33), and attack HAE (I/II) (N=33) plasma. RFU is relative fluorescence units.
Figure 1:
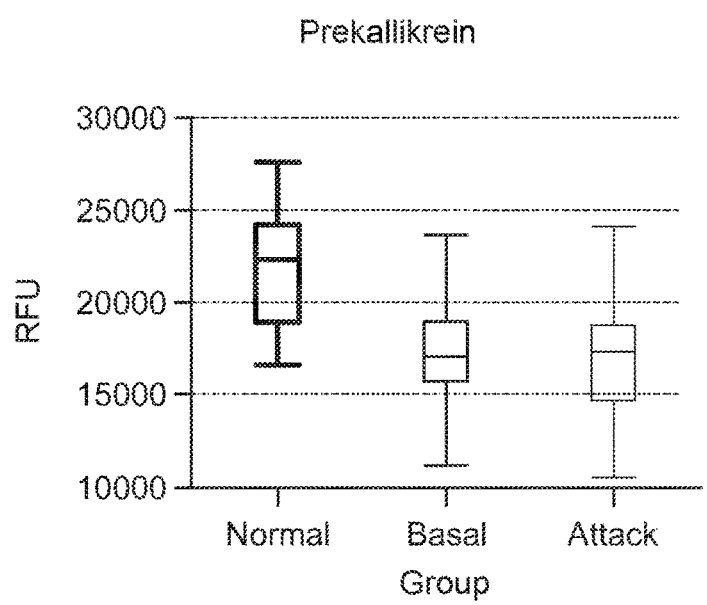

The contact activation system initiates the intrinsic pathway of coagulation and promotes inflammation through the release of the proinflammatory peptide bradykinin. Factor XII (FXII), also known as Hageman Factor, is a serine protease that plays a role in activation of the intrinsic pathways of coagulation as well as the kallikrein-kinin system. FXII is activated by negatively charged surfaces (e.g., polyanionic surfaces, glass, polyphosphate, ellagic acid) to produce the active form FXIIa. Activated FXIIa has the ability to cleave pre-kallikrein, generating active pKal. Subsequently, activated pKal is able to cleave FXII into FXIIa, resulting in a positive feedback loop in which FXIIa generates even more pKal, which further activates additional FXII into FXIIa. Activated pKal is also able to cleave high molecular weight kininogen (HMWK) to release bradykinin. In diseases associated with contact system activation, such as HAE, increased levels of bradykinin can induce vasodilation and inflammation that result in edematous HAE attacks. It is desired to identify novel biomarkers that can be used, for example, to identify diseases as mediated by the contact activation system, identify subjects having or being at risk of having such a disease.

The present disclosure is based, at least in part, on the identification of proteins that are differentially present in biological samples obtained from subjects having diseases associated with the contact activation system (e.g., basal or attack) as compared to healthy individuals via proteomic analysis. It was unexpectedly observed that proteins belonging to particular cellular pathways or processes (e.g., proteins involved in mitochondrial function) and proteins belonging to protein families (e.g., the 7 member protein family) had similar trends (e.g., elevated or reduced levels) in samples from subjects having the disease as compared to healthy individuals.

Accordingly, provided herein are methods for analyzing biological samples from subjects having, suspected of having, or being at risk for a disease associated with the contact activation system (e.g., HAE) by detecting the presence or measuring the level of a protein biomarker set. Such methods may be useful, e.g., for identifying patients who are at risk of a disease associated with the contact activation system (e.g., HAE), selecting a candidate for treatment, monitoring disease progression or disease state, assessing the efficacy of a treatment against a disease, determining a course of treatment, assessing whether a subject is at risk for an attack of the disease, identifying whether a disease or disorder is associated with the contact activation system, and/or for research purposes, including, e.g., studying the mechanism of a disease and/or biological pathways/processes involved in the disease, which may be relied upon for the development of new therapies.

Contact Activation System Protein Biomarkers

The methods and kits described herein are based, at least in part, on the identification of proteins that were found to be differentially present in samples from subjects having HAE as compared with samples from healthy subjects, and/or differentially present in samples from subjects at different stages of such a disease (e.g., basal versus attack) As used herein, the term "protein biomarker" or "protein biomarker set" refers to a protein or set of proteins that are present at different levels in samples from different groups of subjects, for example, subjects having a disease associated with the contact system versus healthy subjects (e.g., subjects who are free of the disease), or subjects having the disease and being at the quiescence stage versus subjects under the attack of the disease. Such biomarker/biomarker sets may be used in both diagnostic/prognostic applications and non-clinical applications (for example, for research purposes).

In some embodiments, a protein biomarker may be present at an elevated level in samples from subjects having a disease associated with the contact activation system (e.g., HAE) as compared to the level of the same protein biomarker in samples from healthy subjects. In some embodiments, a protein biomarker may be present at a reduced level in samples from subjects having a disease associated with the contact activation system (e.g., HAE) as compared to the level of the biomarker in samples from healthy subjects. In yet other instances, a protein biomarker may be present at an elevated level in samples obtained from subjects under attack of a disease as described herein as compared with subjects during disease quiescence. Alternatively, a protein biomarker may be present at a reduced level in samples obtained from subjects under attack of a disease as described herein as compared with subjects during disease quiescence.

In some embodiments, a protein biomarker set containing one or more biomarkers can be analyzed in the methods described herein. When the protein biomarker set contains more than one biomarker, all of the biomarkers may present at elevated levels or reduced levels in subjects having a disease as compared with health subjects. Alternatively, a protein biomarker set may contain at least one biomarker that is elevated in subjects having the disease as compared with healthy subjects and at least one biomarker that is reduced in subjects having the disease as compared with healthy subjects.

Similarly, a protein biomarker set for differentiating subjects under attack of a disease from subjects in disease quiescence, the biomarker set may contain multiple biomarkers that are all elevated or reduced in a first disease stage (e.g., attack) as compared with a second disease stage (e.g., quiescence). Alternatively, the biomarker set may contain at least one biomarker that is elevated in the first disease stage as compared with the second disease stage and at least one biomarker that is reduced in the first disease stage as compared with the second disease stage.

Table 1 below provides markers that can be evaluated by the methods described herein to evaluate subjects or biological samples from subjects for diseases associated with the contact activation system.

In some embodiments, the biomarker set to be measured and analyzed in any of the methods described herein includes at least one (e.g., 1, 2, 3, 4, 5, 6, 7, 8, 9, 10, or more) proteins selected from Table 1. When the biomarker set includes a single protein, that protein may not be complement protein 4 (C4), C1 Inhibitor, prekallikrein, heat-shock protein 90, tissue-type plasminogen activator, or thrombin. In some examples, the protein biomarker set to be measured and analyzed in a method described herein does not include a combination of any one of complement protein 4 (C4), C1 Inhibitor, prekallikrein, heat-shock protein 90, tissue-type plasminogen activator, and thrombin.

As described in Example 1, it was unexpectedly found that several proteins involved in mitochondrial function were differentially present in samples from subjects having HAE as compared to healthy subjects. In some embodiments, the biomarker set includes one or more mitochondrial proteins as listed in Table 1. In some embodiments, the mitochondrial protein biomarker set includes ATP synthase subunit O (ATPO), mitochondrial heat shock protein 60 (HSP60), cyclophilin F (also referred to as cyclophilin D or peptidyl-prolyl ci-trans isomerase F; EC: 5.2.1.8), or a combination thereof.

As also described in Example 1, it was also found that several proteins belonging to a related family of proteins were differentially present in samples from subjects having HAE as compared to healthy subjects. In some embodiments, the biomarker is 14-3-3 zeta/delta or 14-3-3 beta/alpha. In some embodiments, the biomarker is a protein kinase, such as tyrosine protein kinase YES, tyrosine protein kinase LYN, or mitogen-activated protein kinase 14 (MAPK14), or a combination thereof. In some embodiments, the biomarkers are glycogen synthase kinase 3 alpha/beta (GSK-3 alpha/beta). In some embodiments, the biomarker is ATP-dependent RNA helicase DDX19B (DEAD box protein DDX19B). In some embodiments, the biomarker is eukaryotic translation initiation factor 5A-1 (eIF-5A-1). Any combination of these protein biomarkers is also within the scope of the present disclosure.

TABLE 1

Contact System Activation Biomarkers

| Protein | q | p | H | C-Stat | C-Stat Probability | T-Test if means pooled variance | Attack/ Normal | Basal/ Normal | Attack/ Basal |
|---|---|---|---|---|---|---|---|---|---|
| Complement C4 | 6.81E−09 | 5.20E−12 | 5.20E+01 | 0.998 | 6.70E−02 | 2.07E−33 | 0.10 | 0.16 | 0.62 |
| Interleukin-36 alpha (IL-1F6) | 1.07E−08 | 1.63E−11 | 4.97E+01 | 0.986 | 9.80E−05 | 1.53E−13 | 0.19 | 0.24 | 0.78 |
| Eukaryotic translation initiation factor 5A-1 (eIF-5A-1) | 7.80E−04 | 6.91E−05 | 1.92E+01 | 0.947 | 2.19E−05 | 2.93E−05 | 1.36 | 1.41 | 0.96 |

TABLE 1-continued

Contact System Activation Biomarkers

| Protein | q | p | H | C-Stat | C-Stat Probability | T-Test if means pooled variance | Attack/ Normal | Basal/ Normal | Attack/ Basal |
|---|---|---|---|---|---|---|---|---|---|
| 60 kDa heat shock protein, mitochondrial (HSP 60) | 3.00E−07 | 1.12E−09 | 4.12E+01 | 0.938 | 5.22E−05 | 1.16E−06 | 2.88 | 3.77 | 0.76 |
| 14-3-3 protein family | 4.09E−07 | 2.75E−09 | 3.94E+01 | 0.938 | 4.65E−05 | 6.79E−03 | 2.32 | 2.77 | 0.83 |
| ATP-dependent RNA helicase DDX19B (DEAD-box protein 19B) | 3.00E−07 | 1.14E−09 | 4.12E+01 | 0.936 | 4.27E−05 | 2.21E−05 | 1.82 | 2.03 | 0.89 |
| Mitogen-activated protein kinase 14 (MAPK14) | 4.09E−07 | 3.61E−09 | 3.89E+01 | 0.934 | 2.23E−05 | 1.89E−03 | 1.65 | 1.88 | 0.88 |
| Tyrosine-protein kinase Lyn (LYN) | 4.09E−07 | 3.59E−09 | 3.89E+01 | 0.934 | 9.56E−05 | 9.58E−07 | 3.16 | 3.80 | 0.83 |
| Glycogen synthase kinase-3 alpha/beta (GSK-3 alpha/beta) | 4.09E−07 | 3.75E−09 | 3.88E+01 | 0.933 | 2.50E−05 | 7.34E−05 | 2.18 | 2.45 | 0.89 |
| Tyrosine-protein kinase (YES) | 4.09E−07 | 3.37E−09 | 3.90E+01 | 0.933 | 3.79E−05 | 9.96E−04 | 1.36 | 1.54 | 0.88 |
| Mitogen-activated protein kinase 3 (ERK-1) | 5.06E−07 | 6.18E−09 | 3.78E+01 | 0.929 | 1.28E−05 | 1.78E−05 | 1.89 | 2.05 | 0.92 |
| Cytochrome P450 3A4 | 5.06E−07 | 5.69E−09 | 3.80E+01 | 0.928 | 1.27E−05 | 1.27E−05 | 1.66 | 1.89 | 0.88 |
| Protein kinase C alpha type (PKC-A) | 5.06E−07 | 5.99E−09 | 3.79E+01 | 0.927 | 2.80E−05 | 8.36E−06 | 3.79 | 4.40 | 0.86 |
| Tyrosine-protein kinase Lyn, isoform B (LYNB) | 5.06E−07 | 5.93E−09 | 3.79E+01 | 0.927 | 4.92E−05 | 3.73E−08 | 3.09 | 3.59 | 0.86 |
| Complement C2 | 5.41E−07 | 7.02E−09 | 3.75E+01 | 0.922 | 3.90E−06 | 8.45E−14 | 0.61 | 0.68 | 0.90 |
| Tyrosine-protein kinase CSK (CSK) | 8.54E−07 | 1.17E−08 | 3.65E+01 | 0.920 | 2.35E−05 | 4.67E−04 | 3.34 | 3.93 | 0.85 |
| Sorting nexin-4 | 9.51E−07 | 1.38E−08 | 3.62E+01 | 0.919 | 2.89E−05 | 5.03E−05 | 2.36 | 2.62 | 0.90 |
| Small ubiquitin-related modifier 3 (SUMO3) | 2.11E−05 | 1.19E−06 | 2.73E+01 | 0.918 | 6.75E−06 | 1.70E−09 | 1.50 | 1.72 | 0.87 |
| Protein disulfide-isomerase A3 | 1.12E−06 | 1.78E−08 | 3.57E+01 | 0.917 | 2.52E−05 | 2.87E−04 | 1.58 | 1.75 | 0.90 |
| MAP kinase-activated protein kinase 2 (MAPK2) | 1.28E−06 | 2.52E−08 | 3.50E+01 | 0.915 | 1.40E−05 | 6.75E−05 | 2.31 | 2.53 | 0.91 |
| Tyrosine-protein kinase BTK (BTK) | 1.12E−06 | 1.89E−08 | 3.56E+01 | 0.914 | 1.98E−05 | 2.34E−03 | 3.20 | 3.77 | 0.85 |
| EGF-containing fibulin-like extracellular matrix protein 1 (FBLN3) | 4.01E−04 | 3.34E−05 | 2.06E+01 | 0.913 | 1.26E−05 | 2.87E−07 | 1.26 | 1.25 | 1.01 |
| Cyclin-dependent kinase 8:Cyclin-C complex (CDK8/cyclin C) | 1.30E−06 | 2.68E−08 | 3.49E+01 | 0.913 | 2.29E−05 | 2.56E−04 | 1.31 | 1.41 | 0.93 |
| Pyruvate kinase PKM (M2-PK) | 1.28E−06 | 2.50E−08 | 3.50E+01 | 0.912 | 1.86E−05 | 6.82E−05 | 2.70 | 3.01 | 0.89 |
| 14-3-3 protein theta | 3.13E−03 | 3.45E−04 | 1.59E+01 | 0.910 | 2.55E−05 | 1.35E−03 | 1.19 | 1.26 | 0.94 |
| Tyrosine-protein kinase Fer (FER) | 1.62E−06 | 4.21E−08 | 3.40E+01 | 0.908 | 4.12E−05 | 7.68E−04 | 2.79 | 3.15 | 0.89 |
| Tyrosine-protein kinase Fyn (FYN) | 1.49E−06 | 3.74E−08 | 3.42E+01 | 0.908 | 1.22E−04 | 1.20E−04 | 1.88 | 2.08 | 0.91 |
| Heat shock cognate 71 kDa protein (HSP70 protein 8) | 5.62E−03 | 6.99E−04 | 1.45E+01 | 0.906 | 2.28E−05 | 3.88E−06 | 1.23 | 1.29 | 0.95 |
| Peptidyl-prolyl cis-trans isomerase D (PPID) | 1.98E−06 | 5.60E−08 | 3.34E+01 | 0.906 | 7.48E−05 | 6.23E−04 | 3.32 | 3.68 | 0.90 |
| RAC-alpha/beta/gamma serine/threonine-protein kinase (PKB a/b/g) | 1.49E−06 | 3.75E−08 | 3.42E+01 | 0.906 | 2.77E−05 | 2.07E−03 | 1.74 | 2.08 | 0.84 |
| Calcineurin | 1.68E−06 | 4.48E−08 | 3.38E+01 | 0.905 | 6.52E−05 | 4.21E−03 | 1.79 | 2.06 | 0.87 |
| Histone-lysine N-methyltransferase EHMT2 (NG36) | 4.47E−03 | 5.26E−04 | 1.51E+01 | 0.900 | 4.74E−05 | 2.68E−04 | 0.73 | 0.73 | 0.99 |
| Xaa-Pro aminopeptidase 1 (XPNPEP1) | 1.40E−06 | 3.10E−08 | 3.46E+01 | 0.899 | 4.41E−05 | 8.70E−04 | 1.79 | 2.42 | 0.74 |

TABLE 1-continued

Contact System Activation Biomarkers

| Protein | q | p | H | C-Stat | C-Stat Probability | T-Test if means pooled variance | Attack/ Normal | Basal/ Normal | Attack/ Basal |
|---|---|---|---|---|---|---|---|---|---|
| 3-hydroxyacyl-CoA dehydrogenase type-2 (ERAB) | 1.75E−06 | 4.80E−08 | 3.37E+01 | 0.897 | 3.39E−05 | 8.61E−03 | 1.88 | 2.37 | 0.79 |
| Serine/threonine-protein kinase PAK 6 (PAK6) | 3.10E−06 | 1.05E−07 | 3.21E+01 | 0.896 | 6.78E−05 | 1.07E−04 | 3.55 | 3.55 | 1.00 |
| Chloride intracellular channel protein 1 (NCC27) | 2.88E−06 | 8.80E−08 | 3.25E+01 | 0.896 | 1.97E−05 | 3.38E−03 | 2.21 | 2.57 | 0.86 |
| Growth factor receptor-bound protein 2 (GRB2 adapter protein) | 1.28E−06 | 2.49E−08 | 3.50E+01 | 0.895 | 1.31E−04 | 6.14E−04 | 2.66 | 3.23 | 0.82 |
| Sphingosine kinase 1 | 2.91E−06 | 9.55E−08 | 3.23E+01 | 0.894 | 3.34E−05 | 1.32E−04 | 2.45 | 2.80 | 0.88 |
| Methionine aminopeptidase 1 (METAP1) | 2.91E−06 | 9.34E−08 | 3.24E+01 | 0.894 | 7.58E−05 | 3.97E−03 | 1.90 | 2.19 | 0.87 |
| Complement C1r subcomponent | 3.10E−06 | 1.06E−07 | 3.21E+01 | 0.893 | 3.05E−05 | 9.79E−09 | 1.72 | 1.62 | 1.06 |
| Ubiquitin-fold modifier-conjugating enzyme 1 (UFC1) | 2.71E−06 | 8.07E−08 | 3.27E+01 | 0.892 | 2.99E−05 | 1.17E−05 | 1.52 | 1.75 | 0.87 |
| Signal transducer and activator oft ranscription 1-alpha/beta (STAT1) | 4.07E−06 | 1.50E−07 | 3.14E+01 | 0.890 | 4.75E−05 | 5.44E−05 | 2.20 | 2.27 | 0.97 |
| Alpha-enolase | 4.07E−06 | 1.43E−07 | 3.15E+01 | 0.889 | 2.61E−05 | 2.18E−04 | 1.81 | 2.03 | 0.89 |
| Signal transducer and activator of transcription 3 (STAT3) | 4.07E−06 | 1.47E−07 | 3.15E+01 | 0.889 | 1.06E−04 | 3.14E−03 | 1.82 | 2.09 | 0.87 |
| Translationally-controlled tumor protein (TCTP) | 4.07E−06 | 1.52E−07 | 3.14E+01 | 0.888 | 5.11E−05 | 1.24E−03 | 1.93 | 2.24 | 0.86 |
| Mothers against decapentaplegic homolog 3 (SMAD3) | 5.47E−06 | 2.13E−07 | 3.07E+01 | 0.887 | 6.69E−05 | 6.78E−05 | 1.53 | 1.57 | 0.97 |
| beta-adrenergic receptor kinase 1 (BARK1) | 4.53E−06 | 1.73E−07 | 3.11E+01 | 0.887 | 5.28E−05 | 3.47E−04 | 2.07 | 2.34 | 0.88 |
| Mitogen-activated protein kinase 1 (MK01) | 5.68E−06 | 2.25E−07 | 3.06E+01 | 0.886 | 1.11E−04 | 2.67E−04 | 1.82 | 1.89 | 0.97 |
| Mothers against decapentaplegic homolog 2 (SMAD2) | 6.40E−06 | 2.64E−07 | 3.03E+01 | 0.881 | 2.66E−05 | 2.80E−04 | 2.05 | 2.29 | 0.89 |
| CAMP-regulated phosphoprotein 19 (ARP19) | 7.11E−06 | 3.10E−07 | 3.00E+01 | 0.879 | 5.17E−05 | 5.74E−04 | 1.72 | 1.82 | 0.94 |
| Ribosome maturation protein SBDS (SBDS) | 7.50E−06 | 3.32E−07 | 2.98E+01 | 0.879 | 5.76E−05 | 5.27E−04 | 2.00 | 2.23 | 0.90 |
| Dynein light chain roadblock-type 1 (DLRB1) | 6.94E−06 | 2.91E−07 | 3.01E+01 | 0.879 | 4.10E−04 | 8.47E−03 | 1.87 | 2.36 | 0.79 |
| Bcl-2-like protein 1 | 7.96E−06 | 3.65E−07 | 2.96E+01 | 0.876 | 5.45E−05 | 2.85E−04 | 1.23 | 1.38 | 0.89 |
| 14-3-3 protein beta/alpha | 1.02E−05 | 4.73E−07 | 2.91E+01 | 0.876 | 4.66E−05 | 3.93E−03 | 1.77 | 2.00 | 0.88 |
| Eukaryotic translation initiation factor 4 gamma 2 (IF4G2) | 5.89E−06 | 2.38E−07 | 3.05E+01 | 0.875 | 6.94E−05 | 1.18E−03 | 2.49 | 3.33 | 0.75 |
| Dual specificity protein phosphatase 3 (DUS3) | 7.96E−06 | 3.60E−07 | 2.97E+01 | 0.875 | 3.39E−03 | 9.30E−03 | 1.53 | 1.92 | 0.80 |
| Coiled-coil domain-containing protein 80 (URB) | 1.05E−05 | 5.01E−07 | 2.90E+01 | 0.874 | 5.64E−05 | 4.13E−06 | 1.37 | 1.26 | 1.09 |
| Heat shock protein beta-1 (HSP 27) | 1.08E−05 | 5.29E−07 | 2.89E+01 | 0.873 | 4.77E−05 | 4.69E−05 | 2.49 | 2.66 | 0.94 |
| Cofilin-1 (Cofilin-1) | 1.05E−05 | 5.04E−07 | 2.90E+01 | 0.872 | 5.73E−05 | 7.02E−05 | 1.49 | 1.63 | 0.92 |
| 3-phosphoinositide-dependent protein kinase 1 (PDPK1) | 1.24E−05 | 6.34E−07 | 2.85E+01 | 0.871 | 9.29E−05 | 2.61E−03 | 2.00 | 2.29 | 0.87 |

TABLE 1-continued

Contact System Activation Biomarkers

| Protein | q | p | H | C-Stat | C-Stat Probability | T-Test if means pooled variance | Attack/ Normal | Basal/ Normal | Attack/ Basal |
|---|---|---|---|---|---|---|---|---|---|
| Interleukin-17B (IL-17B) | 1.31E−05 | 6.82E−07 | 2.84E+01 | 0.871 | 5.83E−02 | 1.63E−02 | 0.88 | 0.89 | 0.99 |
| Nucleoside diphosphate kinase B (NDP kinase B) | 1.15E−05 | 5.70E−07 | 2.88E+01 | 0.870 | 3.16E−05 | 2.79E−05 | 1.76 | 2.08 | 0.84 |
| Ras-related C3 botulinum toxin substrate 1 (RAC1) | 1.22E−05 | 6.16E−07 | 2.86E+01 | 0.869 | 2.48E−05 | 3.68E−04 | 1.84 | 2.13 | 0.86 |
| Plasma prekallikrein | 2.50E−05 | 1.45E−06 | 2.69E+01 | 0.863 | 7.37E−06 | 4.30E−09 | 0.77 | 0.78 | 0.98 |
| Tyrosine-protein kinase Tec (TEC) | 2.26E−05 | 1.29E−06 | 2.71E+01 | 0.863 | 2.25E−04 | 4.14E−03 | 1.58 | 1.68 | 0.94 |
| Mediator of RNA polymerase II transcription subunit 1 (MED-1) | 9.52E−04 | 8.72E−05 | 1.87E+01 | 0.862 | 5.43E−05 | 4.05E−04 | 0.84 | 0.82 | 1.03 |
| Platelet glycoprotein VI (GPVI) | 2.05E−05 | 1.14E−06 | 2.74E+01 | 0.862 | 3.53E−05 | 8.61E−04 | 1.65 | 1.94 | 0.85 |
| Heat shock protein HSP 90-alpha/beta (HSP 90a/b) | 2.05E−05 | 1.13E−06 | 2.74E+01 | 0.862 | 1.26E−04 | 2.24E−03 | 1.63 | 1.87 | 0.87 |
| Protein kinase C beta type (splice variant beta-II) (PKC-B-II) | 1.37E−06 | 2.92E−08 | 3.47E+01 | 0.858 | 1.35E−04 | 2.25E−03 | 3.42 | 3.99 | 0.86 |
| Glycylpeptide N-tetradecanoyltransferase 1 (NMT1) | 2.86E−05 | 1.71E−06 | 2.66E+01 | 0.857 | 2.72E−04 | 2.26E−04 | 1.68 | 1.77 | 0.95 |
| Beta-Ala-His dipeptidase (CNDP1) | 1.68E−03 | 1.64E−04 | 1.74E+01 | 0.856 | 4.30E−04 | 5.57E−04 | 0.68 | 0.63 | 1.08 |
| Aflatoxin B1 aldehyde reductase member 2 | 2.86E−05 | 1.72E−06 | 2.65E+01 | 0.855 | 1.48E−04 | 1.66E−03 | 1.98 | 2.36 | 0.84 |
| Peptidyl-prolyl cis-trans isomerase A (Cyclophilin A) | 2.99E−05 | 1.82E−06 | 2.64E+01 | 0.855 | 7.84E−05 | 2.10E−05 | 1.44 | 1.54 | 0.94 |
| Thrombopoietin (Tpo) | 9.68E−04 | 8.94E−05 | 1.86E+01 | 0.855 | 1.15E−04 | 3.11E−04 | 1.28 | 1.40 | 0.91 |
| Protein amnionless (AMNLS) | 4.20E−05 | 2.66E−06 | 2.57E+01 | 0.851 | 2.64E−05 | 2.53E−09 | 0.75 | 0.76 | 0.99 |
| Drebrin-like protein (DBNL) | 7.00E−05 | 4.75E−06 | 2.45E+01 | 0.848 | 1.18E−04 | 3.14E−03 | 1.34 | 1.46 | 0.92 |
| Lactadherin (MFGM) | 5.96E−05 | 4.00E−06 | 2.49E+01 | 0.848 | 1.06E−05 | 2.60E−08 | 0.62 | 0.59 | 1.05 |
| Alpha-2-macroglobulin | 5.24E−05 | 3.48E−06 | 2.51E+01 | 0.848 | 6.07E−05 | 4.39E−07 | 0.66 | 0.65 | 1.02 |
| HemK methyltransferase family member 2 (HEMK2) | 5.00E−05 | 3.25E−06 | 2.53E+01 | 0.848 | 2.84E−03 | 1.38E−02 | 1.38 | 1.51 | 0.91 |
| Angiotensinogen | 4.99E−05 | 3.20E−06 | 2.53E+01 | 0.847 | 8.71E−04 | 4.91E−09 | 0.64 | 0.61 | 1.04 |
| Transgelin-2 (Transgelin-2) | 3.13E−04 | 2.51E−05 | 2.12E+01 | 0.847 | 3.22E−03 | 1.63E−02 | 1.38 | 1.60 | 0.86 |
| Tyrosine-protein phosphatase non-receptor type 6 (PTP-1C) | 8.07E−05 | 5.67E−06 | 2.42E+01 | 0.844 | 1.52E−04 | 3.90E−03 | 1.69 | 1.84 | 0.92 |
| Protein kinase C theta type (KPCT) | 5.08E−05 | 3.34E−06 | 2.52E+01 | 0.844 | 2.32E−04 | 1.83E−03 | 1.66 | 1.90 | 0.87 |
| Calpain I | 9.12E−05 | 6.47E−06 | 2.39E+01 | 0.839 | 1.64E−04 | 1.32E−03 | 1.48 | 1.65 | 0.90 |
| Epidermal growth factor receptor (ERBB1) | 9.97E−05 | 7.31E−06 | 2.37E+01 | 0.836 | 5.63E−05 | 1.37E−06 | 0.81 | 0.81 | 1.01 |
| CAMP-dependent protein kinase catalytic subunit alpha (PRKACA) | 1.52E−05 | 8.14E−07 | 2.80E+01 | 0.836 | 8.71E−03 | 4.02E−02 | 1.70 | 2.68 | 0.63 |
| Glyceraldehyde-3-phosphate dehydrogenase (GAPDH, liver) | 9.97E−05 | 7.27E−06 | 2.37E+01 | 0.834 | 3.32E−04 | 1.84E−04 | 1.75 | 1.90 | 0.92 |
| Integrin alpha-I: beta-1 complex (Integrin a1b1) | 1.32E−04 | 9.80E−06 | 2.31E+01 | 0.833 | 3.72E−04 | 2.64E−03 | 1.50 | 1.59 | 0.94 |
| Fibroblast growth factor 17 (FGF-17) | 8.04E−05 | 5.59E−06 | 2.42E+01 | 0.832 | 2.84E−04 | 1.12E−06 | 0.86 | 0.85 | 1.02 |
| Heat shock protein HSP 90-beta (HSP 90b) | 3.51E−05 | 2.20E−06 | 2.61E+01 | 0.831 | 3.46E−04 | 3.72E−04 | 1.47 | 1.57 | 0.93 |

TABLE 1-continued

Contact System Activation Biomarkers

| Protein | q | p | H | C-Stat | C-Stat Probability | T-Test if means pooled variance | Attack/ Normal | Basal/ Normal | Attack/ Basal |
|---|---|---|---|---|---|---|---|---|---|
| Inhibitor of growth protein 1 (ING1) | 1.73E−04 | 1.32E−05 | 2.25E+01 | 0.830 | 3.83E−04 | 4.08E−03 | 1.58 | 1.66 | 0.95 |
| Hsp90 co-chaperone Cdc37 (CDC37) | 1.92E−04 | 1.50E−05 | 2.22E+01 | 0.828 | 6.35E−03 | 1.64E−02 | 1.36 | 1.51 | 0.90 |
| Complement factor D | 1.90E−04 | 1.47E−05 | 2.23E+01 | 0.826 | 1.15E−04 | 8.86E−07 | 1.22 | 1.24 | 0.98 |
| Serotransferrin (Transferrin) | 1.69E−04 | 1.27E−05 | 2.26E+01 | 0.823 | 3.65E−05 | 2.11E−07 | 0.86 | 0.84 | 1.02 |
| Vacuolar protein sorting-associated protein VTA1 homolog (DRG-1) | 2.99E−04 | 2.38E−05 | 2.13E+01 | 0.818 | 9.38E−03 | 6.18E−03 | 1.55 | 1.70 | 0.91 |
| Adapter molecule crk (CRK) | 7.67E−05 | 5.27E−06 | 2.43E+01 | 0.813 | 1.77E−03 | 6.63E−03 | 1.33 | 1.76 | 0.76 |
| Methionine aminopeptidase 2 (AMPM2) | 3.32E−04 | 2.71E−05 | 2.10E+01 | 0.812 | 1.25E−03 | 6.28E−04 | 1.50 | 1.63 | 0.92 |
| Tissue-type plasminogen activator (tPA) | 4.00E−04 | 3.30E−05 | 2.06E+01 | 0.809 | 9.44E−04 | 4.59E−04 | 1.68 | 1.77 | 0.95 |
| Importin subunit beta-1 (IMB1) | 2.17E−04 | 1.71E−05 | 2.20E+01 | 0.806 | 3.15E−02 | 3.92E−02 | 1.49 | 2.15 | 0.69 |
| Calcium/calmodulin-dependent protein kinase type II subunit delta (CAMK2D) | 5.25E−04 | 4.53E−05 | 2.00E+01 | 0.805 | 2.20E−03 | 9.71E−03 | 1.43 | 1.59 | 0.90 |
| Vascular endothelial growth factor receptor 2 (VEGF sR2) | 7.51E−04 | 6.59E−05 | 1.93E+01 | 0.802 | 1.02E−03 | 8.79E−05 | 0.82 | 0.83 | 0.99 |
| Histone deacetylase 8 (HDAC8) | 2.21E−03 | 2.35E−04 | 1.67E+01 | 0.802 | 1.82E−03 | 4.83E−02 | 1.15 | 1.19 | 0.96 |
| Carbonic anhydrase 13 | 4.49E−04 | 3.77E−05 | 2.04E+01 | 0.801 | 3.99E−03 | 2.50E−02 | 1.64 | 2.31 | 0.71 |
| ATP synthase subunit O, mitochondrial (ATPO) | 3.00E−07 | 1.05E−09 | 4.14E+01 | 0.800 | 4.56E−03 | 2.45E−03 | 3.76 | 4.34 | 0.87 |
| Dual specificity mitogen-activated protein kinase 3 (MP2K3) | 4.48E−03 | 5.30E−04 | 1.51E+01 | 0.799 | 1.20E−04 | 7.84E−06 | 1.22 | 1.31 | 0.93 |
| Histone H2A.z | 3.19E−04 | 2.58E−05 | 2.11E+01 | 0.795 | 7.40E−04 | 2.46E−03 | 1.69 | 1.42 | 1.19 |
| Proto-oncogene tyrosine-protein kinase Src (SRCN1) | 1.28E−06 | 2.55E−08 | 3.50E+01 | 0.794 | 3.95E−03 | 9.74E−03 | 3.83 | 3.97 | 0.97 |
| Beta-2-microglobulin | 2.21E−03 | 2.37E−04 | 1.67E+01 | 0.793 | 5.16E−04 | 8.62E−05 | 1.21 | 1.20 | 1.01 |
| Hemoglobin | 8.67E−04 | 7.75E−05 | 1.89E+01 | 0.791 | 4.41E−02 | 3.34E−03 | 0.33 | 0.35 | 0.93 |
| Bone morphogenetic protein receptor type-1A (BMPR1A) | 1.26E−03 | 1.17E−04 | 1.81E+01 | 0.787 | 3.72E−04 | 9.16E−06 | 0.75 | 0.72 | 1.05 |
| Neurogenic locus notch homolog protein 1 (Notch 1) | 1.57E−03 | 1.51E−04 | 1.76E+01 | 0.787 | 6.95E−05 | 1.22E−06 | 0.86 | 0.85 | 1.01 |
| Thrombin | 1.54E−03 | 1.47E−04 | 1.76E+01 | 0.786 | 3.40E−04 | 2.07E−02 | 0.52 | 0.55 | 0.95 |
| Kallistatin | 1.70E−03 | 1.73E−04 | 1.73E+01 | 0.786 | 2.01E−04 | 8.12E−06 | 0.83 | 0.85 | 0.98 |
| A disintegrin and metalloproteinase with thrombospondin motifs 13 (ATS13) | 1.70E−03 | 1.71E−04 | 1.73E+01 | 0.785 | 5.40E−04 | 3.41E−05 | 0.73 | 0.74 | 1.00 |
| Lactoperoxidase (PERL) | 1.69E−03 | 1.67E−04 | 1.74E+01 | 0.784 | 6.52E−04 | 8.40E−05 | 0.67 | 0.73 | 0.91 |
| Eukaryotic translation initiation factor 4H (eIF-4H) | 1.52E−05 | 8.01E−07 | 2.81E+01 | 0.783 | 4.09E−04 | 3.20E−05 | 2.17 | 3.32 | 0.65 |
| Macrophage mannose receptor 1 | 2.17E−03 | 2.28E−04 | 1.68E+01 | 0.782 | 7.38E−04 | 2.04E−04 | 1.21 | 1.17 | 1.03 |
| E3 ubiquitin-protein ligase Mdm2 (MDM2) | 4.79E−04 | 4.06E−05 | 2.02E+01 | 0.781 | 3.63E−03 | 6.30E−03 | 1.14 | 1.30 | 0.88 |
| Superoxide dismutase [Mn], mitochondrial (Mn SOD) | 2.03E−03 | 2.09E−04 | 1.69E+01 | 0.779 | 1.07E−03 | 1.24E−04 | 0.81 | 0.79 | 1.02 |
| C-type lectin domain family 1 member B (CLC1B) | 1.70E−03 | 1.70E−04 | 1.74E+01 | 0.779 | 8.59E−04 | 4.74E−04 | 1.45 | 1.62 | 0.90 |
| Interleukin-17 receptor D (IL-17 RD) | 2.36E−03 | 2.54E−04 | 1.66E+01 | 0.777 | 3.10E−03 | 6.05E−04 | 0.87 | 0.87 | 1.00 |

TABLE 1-continued

Contact System Activation Biomarkers

| Protein | q | p | H | C-Stat | C-Stat Probability | T-Test if means pooled variance | Attack/ Normal | Basal/ Normal | Attack/ Basal |
|---|---|---|---|---|---|---|---|---|---|
| E3 ubiquitin-protein ligase CHIP (CHIP) | 2.17E-03 | 2.29E-04 | 1.68E+01 | 0.775 | 5.84E-02 | 4.07E-02 | 1.36 | 1.58 | 0.86 |
| Hepatocyte growth factor receptor (Met) | 3.13E-03 | 3.49E-04 | 1.59E+01 | 0.772 | 7.58E-04 | 1.26E-04 | 0.84 | 0.83 | 1.01 |
| Sex hormone-binding globulin (SHBG) | 3.87E-03 | 4.40E-04 | 1.55E+01 | 0.770 | 1.80E-04 | 5.82E-07 | 0.41 | 0.43 | 0.96 |
| Caspase-3 | 2.36E-03 | 2.55E-04 | 1.65E+01 | 0.770 | 2.33E-02 | 2.29E-02 | 1.37 | 1.72 | 0.80 |
| Cathepsin L2 (Cathepsin V) | 3.87E-03 | 4.44E-04 | 1.54E+01 | 0.769 | 3.64E-04 | 1.50E-05 | 0.70 | 0.74 | 0.94 |
| Neural cell adhesion molecule 1, 120 kDa isoform (NCAM-120) | 3.68E-03 | 4.13E-04 | 1.56E+01 | 0.769 | 6.59E-04 | 1.22E-04 | 0.80 | 0.80 | 0.99 |
| Insulin-like growth factor-binding protein 6 (IGFBP-6) | 5.63E-03 | 7.10E-04 | 1.45E+01 | 0.766 | 8.96E-04 | 5.00E-04 | 1.17 | 1.17 | 0.99 |
| Interleukin-19 (IL-19) | 5.62E-03 | 6.92E-04 | 1.46E+01 | 0.763 | 4.61E-04 | 7.78E-05 | 0.83 | 0.80 | 1.04 |
| C-type lectin domain family 4 member K (CLC4K) | 5.14E-03 | 6.16E-04 | 1.48E+01 | 0.761 | 9.87E-03 | 4.73E-03 | 0.91 | 0.91 | 1.01 |
| Tropomyosin alpha-4 chain (Tropomyosin 4) | 4.09E-07 | 2.95E-09 | 3.93E+01 | 0.761 | 5.91E-04 | 1.08E-04 | 4.21 | 4.39 | 0.96 |
| Fibronectin Fragment 3 (FN1.3) | 5.45E-03 | 6.66E-04 | 1.46E+01 | 0.759 | 1.65E-03 | 6.75E-04 | 1.35 | 1.34 | 1.01 |
| 14-3-3 protein zeta/delta | 1.12E-06 | 1.79E-08 | 3.57E+01 | 0.758 | 2.43E-03 | 8.35E-04 | 2.22 | 2.28 | 0.97 |
| Dipeptidyl peptidase 2 (DPP2) | 9.74E-03 | 1.38E-03 | 1.32E+01 | 0.757 | 3.56E-03 | 6.71E-04 | 0.86 | 0.85 | 1.01 |
| Phosphoglycerate mutase 1 | 7.04E-03 | 9.14E-04 | 1.40E+01 | 0.757 | 1.11E-02 | 1.20E-02 | 2.49 | 2.56 | 0.97 |
| Interleukin-1 receptor type 2 (IL-1 sRII) | 7.08E-03 | 9.34E-04 | 1.40E+01 | 0.756 | 4.01E-04 | 8.44E-05 | 0.83 | 0.81 | 1.03 |
| Sclerostin (SOST) | 7.82E-03 | 1.06E-03 | 1.37E+01 | 0.755 | 1.33E-03 | 3.73E-04 | 1.60 | 1.40 | 1.15 |
| Insulin-like growth factor-binding protein 1 (IGFBP-1) | 7.08E-03 | 9.34E-04 | 1.40E+01 | 0.755 | 3.37E-03 | 4.27E-04 | 0.37 | 0.40 | 0.94 |
| Roundabout homolog 3 (ROBO3) | 6.83E-03 | 8.81E-04 | 1.41E+01 | 0.755 | 6.67E-02 | 1.54E-02 | 0.81 | 0.77 | 1.04 |
| Fatty acid-binding protein, heart (FABP) | 5.14E-03 | 6.21E-04 | 1.48E+01 | 0.754 | 1.78E-02 | 7.60E-03 | 1.47 | 1.58 | 0.93 |
| Properdin | 6.55E-03 | 8.40E-04 | 1.42E+01 | 0.754 | 1.25E-03 | 1.28E-04 | 1.18 | 1.25 | 0.95 |
| Vascular endothelial growth factor receptor 3 (VEGF sR3) | 7.08E-03 | 9.26E-04 | 1.40E+01 | 0.754 | 5.66E-03 | 2.36E-03 | 0.80 | 0.77 | 1.04 |
| Histone H2B type 2-E (H2B2E) | 4.32E-03 | 5.04E-04 | 1.52E+01 | 0.752 | 2.11E-03 | 1.46E-03 | 1.58 | 1.36 | 1.17 |
| Serine protease HTRA2, mitochondrial (HTRA2) | 2.73E-03 | 2.98E-04 | 1.62E+01 | 0.751 | 2.18E-03 | 1.83E-03 | 1.21 | 1.38 | 0.88 |
| Netrin receptor UNC5D (UNC5H4) | 8.30E-03 | 1.14E-03 | 1.36E+01 | 0.751 | 1.18E-03 | 3.14E-04 | 0.79 | 0.76 | 1.04 |
| Haptoglobin | 9.47E-03 | 1.32E-03 | 1.33E+01 | 0.749 | 1.17E-03 | 3.40E-04 | 3.10 | 2.62 | 1.18 |
| Carbonic anhydrase 6 | 8.15E-03 | 1.11E-03 | 1.36E+01 | 0.746 | 1.97E-03 | 2.88E-05 | 0.54 | 0.49 | 1.09 |
| Complement C4b | 4.58E-03 | 5.46E-04 | 1.50E+01 | 0.741 | 6.25E-03 | 3.06E-03 | 1.54 | 1.86 | 0.83 |
| Tumor necrosis factor-inducible gene 6 protein (TSG-6) | 9.57E-03 | 1.34E-03 | 1.32E+01 | 0.740 | 1.01E-03 | 1.85E-04 | 0.80 | 0.72 | 1.10 |
| Calcium/calmodulin-dependent protein kinase type II subunit alpha (CAMK2A) | 9.10E-03 | 1.26E-03 | 1.34E+01 | 0.728 | 1.44E-02 | 2.92E-02 | 1.13 | 1.29 | 0.88 |
| PIK3CA/PIK3R1 (PIK3CA/PIK3R1) | 9.13E-03 | 1.27E-03 | 1.33E+01 | 0.710 | 2.31E-02 | 2.42E-02 | 1.17 | 1.37 | 0.85 |
| NudC domain-containing protein 3 (NUDC3) | 7.45E-03 | 1.00E-03 | 1.38E+01 | 0.708 | 2.69E-02 | 2.03E-02 | 1.10 | 1.28 | 0.86 |

Utilities of the Protein Biomarkers

One aspect of the present disclosure relates to methods for analyzing samples obtained from subjects (e.g., human patients) having, suspected of having, or being at risk for a disease associated with the contact activation system by measuring the level of a biomarker set as described herein in the sample. Results obtained from such assay methods would be useful for diagnostic and/or prognostic purposes, as well as for other non-clinical purposes, such as research purposes.

(i) Analysis of Biological Samples

The methods described herein involved providing a biological sample obtained from a subject. As used herein, a "biological sample" refers to a composition that comprises tissue, e.g., blood, plasma, or protein, from a subject. A sample includes both an initial unprocessed sample taken from a subject as well as subsequently processed, e.g., partially purified or preserved forms. Exemplary samples include blood, plasma, tears, or mucus. In some embodiments, the sample is a body fluid sample such as a serum or plasma sample. In some embodiments, multiple (e.g., at least 2, 3, 4, 5, or more) biological samples may be collected from subject, over time or at particular time intervals, for example to assess the disease progression or evaluate the efficacy of a treatment.

A biological sample can be obtained from a subject using any means known in the art. In some embodiments, the sample is obtained from the subject by collecting the sample (e.g., a blood sample) into an evacuated collection tube (e.g., an evacuated blood collection tube). In some embodiments, the evacuated collection tube contains one or more protease inhibitors, for example, to reduce or prevent ex vivo activation of the contact system during sample collection. Such protease inhibitors may be contained in a liquid formulation. In some embodiments, the protease inhibitors comprise at least one serine protease inhibitor and at least one cysteine protease inhibitor. Such evacuated collection tubes are known in the art. See, for example, PCT Application No. US2016/046681. Optionally, an evacuated blood collection tube may further comprise one or more anti-coagulants.

The terms "patient," "subject," or "individual" may be used interchangeably and refer to a subject who needs the analysis as described herein. In some embodiments, the subject is a human or a non-human mammal. In some embodiments, a subject is suspected of or is at risk for a disease or disorder associated with the contact activation system (e.g., HAE). Such a subject may exhibit one or more symptoms associated with the disease. Alternatively or in addition, such a subject may carry one or more risk factors for the disease, for example, a genetic factor associated with the disease (e.g., a genetic defect in CI-INH).

Alternatively, the subject who needs the analysis described herein may be a patient of the disease. Such a subject may be under the attack of the disease currently, or may suffer from the disease in the past (e.g., during disease quiescence currently). In some examples, the subject is a human patient who may be on a treatment of the disease, for example, a treatment involving a C1 esterase inhibitor (C1-INH), a plasma kallikrein inhibitor, or a bradykinin inhibitor. In other instances, such a human patient may be free of such a treatment.

Examples of diseases associated with the contact activation system include, without limitation, kallikrein-mediated disorders, e.g., a bradykinin-mediated disorder, such as hereditary angioedema (HAE), non-histamine-dependent idiopathic angioedema, rheumatoid arthritis, Crohn's disease, lupus, Alzheimer's disease, septic shock, burn injury, brain ischemia/reperfusion injury, cerebral edema, diabetic retinopathy, diabetic nephropathy, macular edema, vasculitis, arterial or venous thrombosis, thrombosis associated with ventricular assist devices or stents, heparin-induced thrombocytopenia with thrombosis, thromboembolic disease, and coronary heart disease with unstable angina pectoris, edema, eye disease, gout, intestinal bowel disease, oral mucositis, neuropathic pain, inflammatory pain, spinal stenosis-degenerative spine disease, post-operative ileus, aortic aneurysm, osteoarthritis, hereditary angioedema, pulmonary embolism, stroke, head trauma or peri-tumor brain edema, sepsis, acute middle cerebral artery (MCA) ischemic event (stroke), restenosis (e.g., after angioplasty), systemic lupus erythematosis nephritis, an autoimmune disease, an inflammatory disease, a cardiovascular disease, a neurological disease, a disease associated with protein misfolding, a disease associated with angiogenesis, hypertensive nephropathy and diabetic nephropathy, allergic and respiratory diseases (e.g., anaphylaxis, asthma, chronic obstructive pulmonary disease, acute respiratory distress syndrome, cystic fibrosis, persistent, rhinitis), and tissue injuries (e.g., burn or chemical injury).

In some embodiments, the disease or condition that is associated with the contact activation system is hereditary angioedema (HAE). Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with HAE develop a non-itchy rash called *erythema marginatum* during an attack.

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When HAE is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

C1 inhibitor therapies, as well as other therapies for HAE, are described in Kaplan, A. P., *J Allergy Clin Immunol,* 2010, 126(5):918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert P (CSL Behring), which is pasteurized, was approved by the F.D.A. in 2009 for acute attacks. CINRYZE®, which is nanofiltered, was approved by the F.D.A. in 2008 for prophylaxis. Rhucin/Ruconest (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat *H. pylori* will decrease abdominal attacks.

Newer treatments attack the contact cascade. Ecallantide (KALBITOR®) inhibits plasma kallikrein and has been approved in the U.S. Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., *J Allergy Clin Immunol,* 2010, 126(5):918-925. In type I HAE, the level of C1 inhibitor is decreased, as is the level of C4, whereas C1q level is normal. In type II HAE, the level of C1 inhibitor is normal or increased; however, C1 inhibitor function is abnormal. C4 level is decreased and C1q level is normal. In type III, the levels of C1 inhibitor, C4, and C1q can all be normal. The present disclosure is based, at least in part, on the identification of additional proteins that have differential levels in samples from HAE patients as compared to healthy individuals (Table 1). Measuring the levels of biomarker sets of these proteins can be used to identify whether a subject has a disease, such as HAE. In some embodiments, the methods may be used to determine whether a patient has had or is having an HAE attack.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. *Patient.* 2012; 5(2):113-26.

The biological sample described herein can be subject to analysis by measuring the level of a biomarker set as described herein in the biological sample. Levels (e.g., the amount) of a biomarker disclosed herein, or changes in levels the biomarker, can be assessed using assays described herein and/or assays known in the art. One or more of the biomarkers described herein may be analyzed using convention methods. In some embodiments, the level of a biomarker is assessed or measured by directly detecting the protein in a biological sample. Alternatively or in addition, the level of a protein can be assessed or measured by indirectly in a biological sample, for example, by detecting the level of activity of the protein (e.g. enzymatic assay).

In some embodiments, the biomarker is measured using an immunoassay. Examples of immunoassays include, without limitation immunoblotting assays (Western blots), enzyme linked immunosorbent assays (ELISAs) (e.g., sandwich ELISAs), radioimmunoassays, electrochemiluminescence-based detection assays, magnetic immunoassays, lateral flow assays, and related techniques. Additional suitable immunoassays for detecting a biomarker provided herein will be apparent to those of skill in the art. It will be apparent to those of skill in the art that this disclosure is not limited to immunoassays, however, and that detection assays that are not based on an antibody or an antigen binding antibody fragment, such as mass spectrometry, are also useful for the detection and/or quantification of contact system biomarkers as provided herein. Assays that rely on a chromogenic substrate can also be useful for the detection and/or quantification of contact system biomarkers as provided herein.

The type of detection assay used for the detection and/or quantification of a contact system biomarker such as those provided herein will depend on the particular situation in which the assay is to be used (e.g., clinical or research applications), and on the kind and number of biomarkers to be detected, and on the kind and number of patient samples to be run in parallel, to name a few parameters.

ELISAs are known in the art (see, e.g., Crowther, John R (2009). "The ELISA Guidebook." 2nd ed. Humana Press and Lequin R (2005). "Enzyme immunoassay (EIA)/enzyme-linked immunosorbent assay (ELISA)". *Clin. Chem.* 51 (12): 2415-8) and exemplary ELISAs are described herein. Kits for performing ELISAs are also known in the art and commercially available (see, e.g., ELISA kits from Life Technologies and BD Biosciences).

In some embodiments, an immunoassay is used to measure levels of the protein biomarker(s). The immunoassays described herein may be in the format of a sandwich ELISA, in which a first binding agent that specifically binds a protein of the biomarker set is immobilized on a support member. The support member can then be incubated with a biological sample as described herein for a suitable period of time under conditions that allow for the formation of complex between the binding agent and the protein in the sample. Such a complex can then be detected using a detection agent that binds the protein, the binding agent-protein complex, or the binding agent. The detection agent can be conjugated to a label, which can release a signal directly or indirectly. The intensity of the signal represents the level of the protein in the sample. In some embodiments, the detection agent is detected and its level represents the level of the protein in the sample.

Any binding agent that specifically binds to a desired protein may be used in the methods and kits described herein to measure the level of a protein in a biological sample. In some embodiments, the binding agent is an antibody that specifically binds to a desired protein. In some embodiments, the binding agent is an aptamer antibody that specifically binds to a desired protein. In some embodiments, a sample may be contacted, simultaneously or sequentially, with more than one binding agent that bind different proteins (e.g., multiplexed analysis, for example the SOMAScan™ assay (SOMALogic)). The biological sample is contacted with a binding agent under appropriate conditions. In general, the term "contact" refers to an exposure of the binding agent with the biological sample or agent for a suitable period sufficient for the formation of complexes between the binding agent and the protein in the sample, if any. In some embodiments, the contacting is performed by capillary action in which a biological sample or agent is moved across a surface of the support membrane.

In some embodiments, the immunoassays may be performed on low-throughput platforms, including in single immunoassay format. For example, a low throughput platform may be used to measure the presence and amount of a protein in biological samples (e.g., biological tissues, tissue extracts) for diagnostic methods, monitoring of disease and/or treatment progression, and/or predicting whether a disease or disorder may benefit from a particular treatment.

In some embodiments, it may be necessary to immobilize a binding agent to the support member. Methods for immobilizing a binding agent will depend on factors such as the nature of the binding agent and the material of the support member and may require particular buffers. Such methods will be evident to one of ordinary skill in the art. For example, the biomarker set in a biological sample as described herein may be measured using any of the kits and/or detecting devices which are also described herein.

As used herein, the terms "measuring" or "measurement," or alternatively "detecting" or "detection," means assessing the presence, absence, quantity or amount (which can be an effective amount) of a substance within a sample, including the derivation of qualitative or quantitative concentration levels of such substances, or otherwise evaluating the values or categorization of a subject.

Assays, e.g., Western blot assays, may further involve use of a quantitative imaging system, e.g., LICOR imaging technology, which is commercially available (see, e.g., the Odyssey® CLx infrared imaging system from LI-COR Biosciences). In some embodiments, an electrochemiluminescence detection assay or an assay relying on a combination of electrochemiluminescence and patterned array technology is used (e.g., an ECL or MULTI-ARRAY technology assay from Meso Scale Discovery (MSD)).

In any of the methods described herein, the level of protein of a biomarker set can be compared to the level of the protein in a control sample or a reference sample.

The methods and kits described herein, involving any of the protein biomarker set also described herein, can be applied for the evaluation of a disease associated with the contact activation system, such as those described herein.

(ii) Diagnostic and/or Prognostic Applications

The levels of proteins presented in Table 1 detected in samples from subjects can be used as reliable biomarkers for diagnosing diseases associated with the contact activation system (e.g., HAE), monitoring the progress of such a disease, assessing the efficacy of a treatment for the disease, identifying patients suitable for a particular treatment, and/or predicting disease attack in a subject.

Accordingly, described herein are diagnostic and prognostic methods for a disease associated with the contact activation system based on the level of a biomarker set in a biological sample obtained from a subject. In some embodiments, the level of the biomarker, as measured using any of the methods described herein, can be relied on to evaluate whether a subject (e.g., a human patient) from whom the biological sample is obtained, has or is at risk for a disease associated with the contact activation system, such as a disease associated with plasma kallikrein, e.g., HAE or autoimmune disease such as RA, UC, and Crohn's disease.

In some embodiments, the level of the biomarker can then be compared with a reference sample or a control sample to determine a value indicating the amount of the protein in the sample. In some embodiments, a value for a biomarker is obtained by comparing the level of a protein in a sample to the level of another protein (e.g., an internal control or internal standard) in the sample. Such a biomarker value may be a normalized value over the internal control or internal standard. The value of the biomarker can be compared to a reference value to determine whether the subject has or is at risk for the disease associated with the contact activation system. The reference value may represent the level of the corresponding biomarker in subjects (e.g., human subjects) free of the target disease. In some embodiments, if the level or value of the biomarker is higher than a reference level or value, the subject can be identified as having or at risk for a disease associated with the contact activation system. In some embodiments, if the level or value of the biomarker is lower than a reference level or value, the subject can be identified as having or at risk for a disease associated with the contact activation system.

In some embodiments, the level of the biomarker can be compared to a predetermined threshold for the protein, a deviation from which may indicate the subject has a disease associated with the contact system. The predetermined threshold may represent the value of the biomarker that distinguishes the level of the biomarker in patients having the target disease from the level of the biomarker in patients free of the target disease.

In some embodiments, the biomarker set includes more than one protein, for at least one of which an elevated level indicates the subject has or is at risk of having the disease and for at least one of the proteins a reduced level indicates the subject has or is at risk of having the disease. In some embodiments, the biomarker set includes more than one protein, for each of which an elevated level indicates the subject has or is at risk of having the disease. In some embodiments, the biomarker set includes more than one protein, for each of which a reduced level indicates the subject has or is at risk of having the disease.

In some embodiments, the control sample or reference sample is a biological sample obtained from a healthy individual. In some embodiments, the control sample or reference sample contains a known amount of the protein to be assessed. In some embodiments, the control sample or reference samples is a biological sample obtained from a control subject.

As used herein, a control subject may be a healthy individual, i.e., an individual that is apparently free of the target disease (e.g., a disease associated with the contact system) at the time the level of the protein(s) is measured or has no history of the disease. A control subject may also represent a population of healthy subjects, who preferably would have matches features (e.g., age, gender, ethnic group) as the subject being analyzed by a method described herein.

The control level can be a predetermined level or threshold. Such a predetermined level can represent the level of the protein in a population of subjects that do not have or are not at risk for the target disease (e.g., the average level in the population of healthy subjects). It can also represent the level of the protein in a population of subjects that have the target disease.

The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of the protein in a control population.

The control level as described herein can be determined by routine technology. In some examples, the control level can be obtained by performing a conventional method (e.g., the same assay for obtaining the level of the protein a test sample as described herein) on a control sample as also described herein. In other examples, levels of the protein can be obtained from members of a control population and the results can be analyzed by, e.g., a computational program, to obtain the control level (a predetermined level) that represents the level of the protein in the control population.

By comparing the level of a biomarker in a sample obtained from a candidate subject to the reference value as described herein, it can be determined as to whether the candidate subject has or is at risk for a disease associated with the contact system (e.g., HAE). For example, if the level of biomarker(s) in a sample of the candidate subject deviates from the reference value (e.g., increased as compared to the reference value), the candidate subject might be identified as having or at risk for the disease. When the reference value represents the value range of the level of the biomarker in a population of subjects that have the target disease, the value of biomarker in a sample of a candidate falling in the range indicates that the candidate subject has or is at risk for the target disease.

As used herein, "an elevated level" or "a level above a reference value" means that the level of the biomarker is higher than a reference value, such as a pre-determined threshold of a level the biomarker in a control sample. Control levels are described in detail herein. An elevated level of a biomarker includes a level of the biomarker that is, for example, 1%, 5%, 10%, 20%, 30%, 40%, 50%, 60%, 70%, 80%, 90%, 100%, 150%, 200%, 300%, 400%, 500% or more above a reference value. In some embodiments, the level of the biomarker in the test sample is at least 1.1, 1.2, 1.3, 1.4, 15, 1.6, 1.7, 1.8, 1.9, 2, 2.5, 3, 3.5, 4, 4.5, 5, 5, 6, 7, 8, 9, 10, 50, 100, 150, 200, 300, 400, 500, 1000, 10000-fold or higher than the level of the biomarker in a reference sample.

As used herein, "a decreased level" or "a level below a reference value" means that the level of the biomarker is lower than a reference value, such as a pre-determined threshold of the biomarker in a control sample. Control levels are described in detail herein. A decreased level of the biomarker includes a level of the biomarker that is, for example, 1%, 5%, 10%, 20%, 30%, 40%, 50%, 60%, 70%, 80%, 90%, 100%, 150%, 200%, 300%, 400%, 500% or more lower than a reference value. In some embodiments, the level of the biomarker in the test sample is at least 1.1, 1.2, 1.3, 1.4, 15, 1.6, 1.7, 1.8, 1.9, 2, 2.5, 3, 3.5, 4, 4.5, 5, 5, 6, 7, 8, 9, 10, 50, 100, 150, 200, 300, 400, 500, 1000, 10000-fold or lower than the level of the biomarker in a reference sample.

In some embodiments, the candidate subject is a human patient having a symptom of a disease associated with the contact activation system, such as a pKal-mediated disorder, e.g., HAE or an autoimmune disease such as RA, UC, and Crohn's disease. For example, the subject has edema, swelling wherein said swelling is completely or predominantly peripheral; hives; redness, pain, and swelling in the absence of evidence of infection; non-histamine-mediated edema, recurrent attacks of swelling, or a combination thereof. In other embodiments, the subject has no symptom of a pKal-mediated disorder at the time the sample is collected, has no history of a symptom of a pKal-mediated disorder, or no history of a pKal-mediated disorder such as HAE. In yet other embodiments, the subject is resistant to an antihistamine therapy, a corticosteroid therapy, or both.

A subject identified in the methods described herein may be subject to a suitable treatment, such as treatment with a pKal inhibitor, as described herein.

The assay methods and kits described herein also can be applied for evaluation of the efficacy of a treatment for a disease associated with the contact system, such as those described herein, given the correlation between the level of the biomarkers and such diseases. For examples, multiple biological samples (e.g., blood or plasma samples) can be collected from a subject to whom a treatment is performed either before and after the treatment or during the course of the treatment. The levels of a biomarker can be measured by any of the assay methods as described herein and values (e.g., amounts) of a biomarker can be determined accordingly. For example, if an elevated level of a biomarker indicates that a subject has a target disease and the level of the biomarker decreases after the treatment or over the course of the treatment (the level of the biomarker in a later collected sample as compared to that in an earlier collected sample), it indicates that the treatment is effective. As another example, if a reduced level of a biomarker indicates that a subject has a target disease and the level of the biomarker increases after the treatment or over the course of the treatment (the level of the biomarker in a later collected sample as compared to that in an earlier collected sample), it indicates that the treatment is effective. In some examples, the treatment involves an effective amount of a therapeutic agent, such as a plasma kallikrein inhibitor, a bradykinin B2 receptor antagonist, or a C1 esterase inhibitor (C1-INH). Examples of the therapeutic agents include, but not limited to, lanadelumab, ecallantide, icatibant, and human plasma-derived C1-INH.

If the subject is identified as not responsive to the treatment, a higher dose and/or frequency of dosage of the therapeutic agent are administered to the subject identified.

In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

In other embodiments, the values of a biomarker or biomarker set can also be relied on to identify that a disorder is associated with the contact system or that the disorder may be treatable, for example, by a pKal inhibitor. To practice this method, the level of a biomarker in a sample collected from a subject (e.g., a blood sample or a plasma sample) having a target disease can be measured by a suitable method, e.g., those described herein such as a Western blot or ELISA assay. If the level of the biomarker deviates from the reference value (e.g., elevated or decreased), it indicates that a pKal inhibitor may be effective in treating the disease. If the disease is identified as being susceptible (can be treated by) to a pKal inhibitor, the method can further comprise administering to the subject having the disease an effective amount of a pKal inhibitor, such as an anti-pKal antibody or an inhibitory peptide (e.g., lanadelumab, ecallantide); a bradykinin 2 receptor inhibitor (e.g., icatibant); and/or a C1-INH (e.g. human plasma-derived C1-INH).

Also within the scope of the present disclosure are methods of evaluating the severity of a disease associated with the contact system or the disease state. For example, as described herein, HAE may be in the quiescent state (basal state), during which the subject does not experience symptoms of the disease. HAE attacks are typically recurrent episodes in which the subject may experience pain and swelling, for example in the hands, feet, face, gastrointestinal tract, genitals, and larynx (throat) that can last from two to five days. In some embodiments, the level of one or more biomarker is indicative of whether the subject will experience, is experiencing, or will soon experience an HAE attack. In some embodiments, the methods involve comparing the level of a biomarker in a sample obtained from a subjecting having HAE to the level of the biomarker in a sample from the same subject, for example a sample obtained from the same subject at basal state or a sample obtained from the same subject during a HAE attack.

(iii) Non-Clinical Applications

Further, levels of any of the biomarker set described herein may be used for research purposes. Although many diseases associated with the contact activation system have been identified, it is possible that other diseases are mediated by similar mechanisms or involve similar components. In some embodiments, the methods described herein may be used to identify a disease as being associated with the contact activation system or with components of the contact activation system. In some embodiments, the methods described herein may be used to study mechanisms (e.g., the discovery of novel biological pathways or processes involved in disease development) or progression of a disease.

In some embodiments, the levels of biomarker sets, as described herein, may be relied on in the development of new therapeutics for a disease associated with the contact activation system. For example, the levels of a biomarker set may be measured in samples obtained from a subject having been administered a new therapy (e.g., a clinical trial). In some embodiments, the level of the biomarker set may indicate the efficacy of the new therapeutic or the progression of the disease in the subject prior to, during, or after the new therapy.

Kits and Detecting Devices for Measuring Protein Biomarker Sets

The present disclosure also provides kits and detecting devices for use in measuring the level of a biomarker set as described herein. Such a kit or detecting device can comprise binding agents that specifically bind to protein biomarkers, such as those listed in Table 1. For example, such a kit or detecting device may comprise at least two binding agents that are specific to two different protein biomarkers selected from Table 1. In some instances, the kit or detecting device comprises binding agents specific to all members of the protein biomarker set described herein.

In some embodiments, one or more of the binding agents is an antibody that specifically binds to a protein of the biomarker set. In some embodiments, the one or more binding agents is an aptamer, such as a peptide aptamer or oligonucleotide aptamer, that specifically binds to a protein of the biomarker set.

In some embodiments, the kits further comprise a detection agent (e.g., an antibody binding to the binding agent) for detecting binding of the agent to the protein(s) of the biomarker set. The detection agent can be conjugated to a label. In some embodiments, the detection agent is an antibody that specifically binds to at least one of the binding agents. In some embodiments, the binding agent comprises a tag that can be identified and, directly or indirectly, bound by a detection agent.

In some embodiments, the support member is a membrane, such as a nitrocellulose membrane, a polyvinylidene fluoride (PVDF) membrane, or a cellulose acetate membrane. In some examples, the immunoassay may be in a Western blot assay format or a lateral flow assay format.

In some embodiments, the support member is a multi-well plate, such as an ELISA plate. In some embodiments, the immunoassays described herein can be carried out on high throughput platforms. In some embodiments, multi-well plates, e.g., 24-, 48-, 96-, 384- or greater well plates, may be used for high throughput immunoassays. Individual immunoassays can be carried out in each well in parallel. Therefore, it is generally desirable to use a plate reader to measure multiple wells in parallel to increase assay throughput. In some embodiments, plate readers that are capable of imaging multi-wells (e.g., 4, 16, 24, 48, 96, 384, or greater wells) in parallel can be used for this platform. For example, a commercially available plate reader (e.g., the plate:vision system available from Perkin Elmer, Waltham, Mass.) may be used. This plate reader is capable of kinetic-based fluorescence analysis. The plate:vision system has high collection efficiency optics and has special optics designed for the analysis of 96 wells in parallel. Additional suitable parallel plate readers include but are not limited to the SAFIRE (Tecan, San Jose, Calif.), the FLIPRTETRA® (Molecular Devices, Union City, Calif.), the FDSS7000 (Hamamatsu, Bridgewater, N.J.), and the CellLux (Perkin Elmer, Waltham, Mass.).

In the kit or detecting device, one or more of the binding agents may be immobilized on a support member, e.g., a membrane, a bead, a slide, or a multi-well plate. Selection of an appropriate support member for the immunoassay will depend on various factor such as the number of samples and method of detecting the signal released from label conjugated to the second agent.

The kit can also comprise one or more buffers as described herein but not limited to a coating buffer, a blocking buffer, a wash buffer, and/or a stopping buffer.

In some embodiments, the kit can comprise instructions for use in accordance with any of the methods described herein. The included instructions can comprise a description of how to use the components contained in the kit for measuring the level of proteins of a biomarker set in a biological sample collected from a subject, such as a human patient.

The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of proteins of a biomarker set. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above.

Treatment of Diseases Associated with Contact Activation System

A subject at risk for or suffering from a disease associated with the contact activation system, as identified using the methods described herein, may be treated with any appropriate therapeutic agent. In some embodiments, provided methods include selecting a treatment for a subject based on the output of the described method, e.g., measuring the level of a biomarker set.

In some embodiments, the method comprises one or both of selecting or administering a therapeutic agent, e.g., a kallikrein inhibitor, a bradykinin B2 receptor inhibitor, and/or a C1 esterase inhibitor, for administration to the subject based on the output of the assay, e.g., biomarker detection.

In some embodiments, the therapeutic agent is administered one or more times to the subject. In some embodiments, a plasma kallikrein inhibitor is administered to a subject. In some embodiments, kallikrein inhibitor is a peptide, a small molecule inhibitor, a kallikrein antibody, or a fragment thereof. In some embodiments, an antagonist of bradykinin B2 receptor is administered to a subject. In some embodiments, a C1-INH is administered to a subject.

The therapeutic agent, e.g., kallikrein inhibitor, bradykinin B2 receptor inhibitor, and/or C1-INH, may be administered along with another therapy as part of a combination therapy for treatment of the disease or condition that involves the contact activation system. Combination therapy, e.g., with one or more of a kallikrein inhibitor, bradykinin B2 receptor antagonist, or C1-INH replacement agent, e.g., with one or more of a kallikrein inhibitor, bradykinin B2 receptor antagonist or C1-INH replacement agent and another therapy, may be provided in multiple different configurations. The first agent may be administered before or after the administration of the other therapy. In some situations, the first agent and another therapy (e.g., a therapeutic agent) are administered concurrently, or in close temporal proximity (e.g., a short time interval between the injections, such as during the same treatment session). The first agent and the other therapy may also be administered at greater temporal intervals.

Therapeutic Agents

Plasma kallikrein binding agents (e.g., binding proteins, e.g., polypeptides, e.g., inhibitory polypeptides, e.g., antibodies, e.g., inhibitory antibodies, or other binding agents, e.g., small molecules) are useful therapeutic agents for a variety of diseases and conditions, e.g., diseases and conditions that involve plasma kallikrein activity. For example, in some embodiments, the disease or condition that involves plasma kallikrein activity is hereditary angioedema (HAE). In some embodiments a plasma kallikrein binding agent such as a plasma kallikrein inhibitor is administered to a subject at risk or suffering from a disease associated with the contact activation system.

A number of useful protein inhibitors of kallikrein, either tissue and/or plasma kallikrein, include a Kunitz domain. As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., *Protein Engineering* (1990) 3(7):591-598; Hynes et al., *Biochemistry* (1990) 29:10018-10022) are known. At least eighty one Kunitz domain sequences are known. Known human homologues include three Kunitz domains of LACI also known as tissue factor pathway inhibitor (TFPI) (Wun et al., *J. Biol. Chem.* (1988) 263(13):6001-6004; Girard et al., *Nature* (1989) 338:518-20; Novotny et al, *J. Biol. Chem.* (1989) 264(31):18832-18837) two Kunitz domains of Inter-α-Trypsin Inhibitor, APP-I (Kido et al. *J. Biol. Chem.* (1988) 263(34):18104-18107), a Kunitz domain from collagen, three Kunitz domains of TFPI-2 (Sprecher et al., *PNAS USA* (1994) 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.:

2004-0152633. LACI is a human serum phosphoglycoprotein with a molecular weight of 39 kDa (amino acid sequence in Table 2) containing three Kunitz domains.

TABLE 2

Exemplary Natural Kunitz Domains

```
LACI        1 MIYTMKKVHA LWASVCLLLN LAPAPLNAds eedeehtiit dtelpplklM
(SEQ ID    51 HSFCAFKADD GPCKAIMKRF FFNIFTRQCE EFIYGGCEGN QNRFESLEEC
NO: 1)    101 KKMCTRDnan riikttlqqe kpdfCfleed pqiCrqyitr yfynnqtkqC
          151 erfkyggClg nmnnfetlee CkniCedgpn gfqvdnygtq lnavnnsltp
          201 qstkvpslfe fhgpswCltp adrglCrane nrfyynsvig kCrpfkysgC
          251 ggnennftsk qeClraCkkg fiqriskggl iktkrkrkkq rvkiayeeif
          301 vknm
          The signal sequence (1-28) is uppercase and
          underscored
          LACI-K1 (50-107) is uppercase
          LACI-K2 (121-178) is underscored
          LACI-K3 (211-270) is bold BPTI                 1         2         3         4         5
(SEQ ID    1234567890123456789012345678901234567890123456789012345678
NO: 2)     RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (*J. Biol. Chem.* (1988) 263(13):6001-6004). Girard et al. (*Nature* (1989) 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

Proteins Containing Exemplary Kunitz Domains Include the Following, with SWISS-PROT Accession Numbers in Parentheses:

A4_HUMAN (P05067), A4_MACFA (P53601), A4_MACMU (P29216), A4_MOUSE (P12023), A4_RAT (P08592), A4_SAISC (Q95241), AMBP_PLEPL (P36992), APP2_HUMAN (Q06481), APP2_RAT (P15943), AXP1_ANTAF (P81547), AXP2_ANTAF (P81548), BPT1_BOVIN (P00974), BPT2_BOVIN (P04815), CA17_HUMAN (Q02388), CA36_CHICK (P15989), CA36_HUMAN (P12111), CRPT_BOOMI (P81162), ELAC_MACEU (062845), ELAC_TRIVU (Q29143), EPPI_HUMAN (095925), EPPI_MOUSE (Q9DA01), HTIB_MANSE (P26227), IBP_CARCR (P00993), IBPC_BOVIN (P00976), IBPI_TACTR (P16044), IBPS_BOVIN (P00975), ICS3_BOMMO (P07481), IMAP_DROFU (P11424), IP52_ANESU (P10280), ISC1_BOMMO (P10831), ISC2_BOMMO (P10832), ISH1_STOHE (P31713), ISH2_STOHE (P81129), ISIK_HELPO (P00994), ISP2_GALME (P81906), IVB1_BUNFA (P25660), IVB1_BUNMU (P00987), IVB1_VIPAA (P00991), IVB2_BUNMU (P00989), IVB2_DABRU (P00990), IVB2_HEMHA (P00985), IVB2_NAJNI (P00986), IVB3_VIPAA (P00992), IVBB_DENPO (P00983), IVBC_NAJNA (P19859), IVBC_OPHHA (P82966), IVBE_DENPO (P00984), IVBI_DENAN (P00980), IVBI_DENPO (P00979), IVBK_DENAN (P00982), IVBK_DENPO (P00981), IVBT_ERIMA (P24541), IVBT_NAJNA (P20229), MCPI_MELCP (P82968), SBPI_SARBU (P26228), SPT3_HUMAN (P49223), TKD1_BOVIN (Q28201), TKD1_SHEEP (Q29428), TXCA_DENAN (P81658), UPTI_PIG (Q29100), AMBP_BOVIN (P00978), AMBP_HUMAN (P02760), AMBP_MERUN (Q62577), AMBP_MESAU (Q60559), AMBP_MOUSE (Q07456), AMBP_PIG (P04366), AMBP_RAT (Q64240), IATR_HORSE (P04365), IATR_SHEEP (P13371), SPT1_HUMAN (043278), SPT1_MOUSE (Q9R097), SPT2_HUMAN (043291), SPT2_MOUSE (Q9WU03), TFP2_HUMAN (P48307), TFP2_MOUSE (035536), TFPI_HUMAN (P10646), TFPI_MACMU (Q28864), TFPI_MOUSE (054819), TFPI_RABIT (P19761), TFPI_RAT (Q02445), YN81_CAEEL (Q03610)

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda Md.), e.g., using BLAST; against Pfam database of HMMs (Hidden Markov Models) (e.g., using default parameters for Pfam searching; against the SMART database; or against the ProDom database. For example, the Pfam Accession Number PF00014 of Pfam Release 9 provides numerous Kunitz domains and an HMM for identify Kunitz domains. A description of the Pfam database can be found in Sonhammer et al. *Proteins* (1997) 28(3):405-420 and a detailed description of HMMs can be found, for example, in Gribskov et al. *Meth. Enzymol.* (1990) 183:146-159; Gribskov et al. *Proc. Natl. Acad. Sci.* USA (1987) 84:4355-4358; Krogh et al. *J. Mol. Biol.* (1994) 235:1501-1531; and Stultz et al. *Protein Sci.* (1993) 2:305-314. The SMART database (Simple Modular Architecture Research Tool, EMBL, Heidelberg, DE) of HMMs as described in Schultz et al. *Proc. Natl. Acad. Sci.* USA (1998) 95:5857 and Schultz et al. *Nucl. Acids Res* (2000) 28:231. The SMART database contains domains identified by profiling with the hidden Markov models of the HMMer2 search program (R. Durbin et al. (1998) *Biological sequence analysis: probabilistic models of proteins and nucleic acids.* Cambridge University Press). The database also is annotated and monitored. The ProDom protein domain database consists of an automatic compilation of homologous domains (Corpet et al. *Nucl. Acids Res.* (1999) 27:263-267). Current versions of ProDom are built using recursive PSI-BLAST searches (Altschul et al. *Nucleic Acids Res.* (1997) 25:3389-3402; Gouzy et al. *Computers and Chemistry* (1999) 23:333-340) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. (2002) 30:235-238.

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., *Nature* (1989) 338:518-520). Variants of Kunitz domain 1 of LACI described herein have been screened, isolated and bind kallikrein with enhanced affinity and specificity (see, for example, U.S. Pat. Nos. 5,795,865 and 6,057,287). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

In some aspects, the plasma kallikrein inhibitor binds to the active form of plasma kallikrein. In some embodiments, the plasma kallikrein inhibitor, binds to and inhibits plasma kallikrein, e.g., human plasma kallikrein and/or murine kallikrein. Exemplary polypeptide plasma kallikrein agents are disclosed in U.S. Pat. Nos. 5,795,865, 5,994,125, 6,057,287, 6,333,402, 7,628,983, and 8,283,321, 7,064,107, 7,276,480, 7,851,442, 8,124,586, 7,811,991, and U.S. Publication No. 20110086801, the entire contents of each of which is incorporated herein by reference. In some embodiments, the plasma kallikrein inhibitor is an inhibitory polypeptide or peptide. In some embodiments, the inhibitory peptide is ecallantide (also referred to as DX-88 or KALBITOR®; SEQ ID NO: 3). In some embodiments, the kallikrein inhibitor comprises or consists of an about 58-amino acid sequence of amino acids 3-60 of SEQ ID NO:3 or the DX-88 polypeptide having the 60-amino acid sequence of SEQ ID NO: 3.

Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO: 3).

Plasma kallikrein inhibitor can be full-length antibodies (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')2 or scFv fragment). The binding protein can include two heavy chain immunoglobulins and two light chain immunoglobulins, or can be a single chain antibody. Plasma kallikrein inhibitor can be recombinant proteins such as humanized, CDR grafted, chimeric, deimmunized, or in vitro generated antibodies, and may optionally include constant regions derived from human germline immunoglobulin sequences. In one embodiment, the plasma kallikrein inhibitor is a monoclonal antibody.

Exemplary plasma kallikrein binding proteins are disclosed in U.S. Publication No. 20120201756, the entire contents of which are incorporated herein by reference. In some embodiments, the kallikrein binding protein is an antibody (e.g., a human antibody) having the light and/or heavy chains of antibodies selected from the group consisting of M162-A04, M160-G12, M142-H08, X63-G06, X101-A01 (also referred to as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01 (also referred to herein as DX-2930 or lanadelumab), X115-G04, M29-D09, M145-D11, M06-D09 and M35-G04. In some embodiments, the plasma kallikrein binding protein competes with or binds the same epitope as M162-A04, M160-G12, M142-H08, X63-G06, X101-A01 (also referred to herein as DX-2922), X81-B01, X67-D03, X67-G04, X81-B01, X67-D03, X67-G04, X115-B07, X115-D05, X115-E09, X115-H06, X115-A03, X115-D01, X115-F02, X124-G01, X115-G04, M29-D09, M145-D11, M06-D09 and M35-G04. In some embodiments, the plasma kallikrein binding protein is lanadelumab. See US Publication No. 20110200611 and US Publication No. 20120201756, which are incorporated by reference herein.

An example of a plasma kallikrein inhibitory antibody is lanadelumab. The amino acid sequences of the heavy chain and light chain variable regions of lanadelumab are provided below with the CDR regions identified in boldface and underlined.

Lanadelumab heavy chain variable region sequence (SEQ ID NO: 4)
EVQLLESGGG LVQPGGSLRL SCAASGFTFS HYIMMWVRQA PGKGLEWVSG IYSSGGITVY ADSVKGRFTI SRDNSKNTLY LQMNSLRAED TAVYYCAYRR IGVPRRDEFD IWGQGTMVTV SS Lanadelumab light chain variable region sequence (SEQ ID NO: 5)
DIQMTQSPS TLSASVGDRV TITCRASQSI SSWLAWYQQK PGKAPKLLIY KASTLESGVP SRFSGSGSGT EFTLTISSLQ PDDFATYYCQ QYNTYWTFGQ GTKVEI In some embodiments, a plasma kallikrein inhibitor can have about 85%, 90%, 91%, 92%, 93%, 94%, 95%, 96%, 97%, 98%, 99% or higher sequence identity to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the HC and/or LC framework regions (e.g., HC and/or LC FR 1, 2, 3, and/or 4) to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the HC and/or LC CDRs (e.g., HC and/or LC CDR1, 2, and/or 3) to a plasma kallikrein inhibitor described herein. In some embodiments, a plasma kallikrein inhibitor can have about 85%, 90%, 91%, 92%, 93%, 94%, 95%, 96%, 97%, 98%, 99% or higher sequence identity in the constant region (e.g., CH1, CH2, CH3, and/or CL1) to a plasma kallikrein inhibitor described herein.

In some aspects, a small molecule binds and inhibits the active form of plasma kallikrein.

Bradykinin B2 Receptor Inhibitors

In some embodiments, a bradykinin B2 receptor inhibitor (e.g., antagonist) is administered to a subject. Exemplary bradykinin B2 receptor antagonists include icatibant (Firazyr®), which is a peptidomimetic drug containing 10 amino acids which block binding of native bradykinin to the bradykinin B2 receptor.

C1-INH Replacement Agents

In some embodiment, a C1 esterase inhibitor (C1-INH), such as a replacement C1-INH agent is administered to a subject. Exemplary C1-INH replacement agents are publicly available and include, for example, human plasma-derived C1-INH, e.g. Berinert® and CINRYZE®.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Identification of Proteins Differentially Present in Samples from HAE Patients Compared to Healthy Individuals Plasma samples were collected from healthy individuals (N=22, referred to as "normal" samples) and from patients with HAE (type I/type II) during disease quiescence (N=33, referred to as "basal") and during an attack (N=33, referred to as "attack"). A rigid blood collection protocol was followed in which blood was collected by venipuncture using butterfly needles, plastic catheters, and plastic collection tubes. The first blood collection tube was a serum tube, which was discarded. The second blood collection tube (P100 tube), containing a protease inhibitor cocktail and anticoagulants, was used for the proteomic analysis. Blood collected in the P100 tube was processed to plasma within 1 hour of collection, split into several aliquots, and frozen at <−70° C.

The plasma samples were analyzed using a multiplexed assay capable of detecting relative abundances of 1,310 different human proteins (SOMAscan™ assay; SomaLogic; Boulder, Colo.). This assay compared the signal levels for each of the 1,310 proteins for the three different samples types (healthy individuals, patients having HAE at a quiescent state, and patients having an HAE attack).

Statistical analysis was performed on the data using Kruskal-Wallis analysis of variance. This is a non-parametric method of testing distribution of more than two groups that can have the same or different sample sizes. If the assumption is that scaled distributions are identical for all groups, except for any difference in medians, then the null hypothesis is that the medians of all groups are equal, and the alternative hypothesis is that population median of one group is different than the population median of at least one other group. If the statistic does not show significance, then there is no evidence of stochastic dominance between the samples. However, if there is significance in the median value then at least one sample stochastically dominates another sample.

Protein levels that differed between HAE patients (basal or attack) as compared to healthy individuals with a false positive rate (q value)<0.01 and a T test (p value<0.05, means of pooled variance) are listed in Table 1. The proteins are ranked according to the C-statistic value from receiver operator curve (ROC) analysis, where C-statistic values approaching 1.0 have the highest specificity and sensitivity towards positive detection of HAE (I/II). HAE type I patients are identified as having at least 50% (usually less than 30%) of the normal amount of total C1 inhibitor protein (C1-INH) (David-Lorton, M. *J. Drugs Dermatol*. (2015) 14: 151-157). HAE type II patients have a mutation in the SERPING1 gene that leads to dysfunctional C1-INH protein and are identified as having at least 50% of the normal amount of functional C1-INH. In this study, the HAE patients were not determined as to whether they had type I or type II HAE.

As shown in Table 1, 152 proteins were found to have levels that were statistically different (P<0.05) between plasma samples obtained from HAE patients (attack or basal) and plasma samples obtained from healthy individuals, representing biomarkers that may be assessed to distinguish individuals having HAE from individuals without the disease. The proteomic analysis identified 58 proteins that had levels>2-fold higher in plasma samples from HAE patients (P<0.050) and 12 proteins that had levels>2-fold lower in plasma samples from HAE patients (P<0.05) as compared to samples from healthy individuals. Ten proteins were identified that had C-statistic values>0.93. These proteins, for example, those having high C-statistic values (e.g., >0.9) can be used as reliable biomarkers for HAE and other diseases associated with the contact system, either taken alone or in combination.

Plasma samples from HAE patients contained significantly lower amounts of complement protein 4 ("C4") than plasma from healthy individuals (FIG. 1, panel A). Low C4 levels are used in the clinical diagnosis of HAE (I/II) (Davis-Lorton, M. *J. Drugs Dermatol*. (2015) 14: 151-157). In addition, a slight decrease in the amount of prekallikrein was observed in samples from HAE patients relative to samples from healthy individuals (FIG. 1, panel B). The amount of prekallikrein has also been previously shown to be decreased in HAE patients relative to normal levels. The observed changes in the abundance of C4 and pKal in HAE patients relative to that of healthy individuals using the methods described herein indicates the methods are able to detect alterations in protein levels relevant to disease onset.

Figure 2:
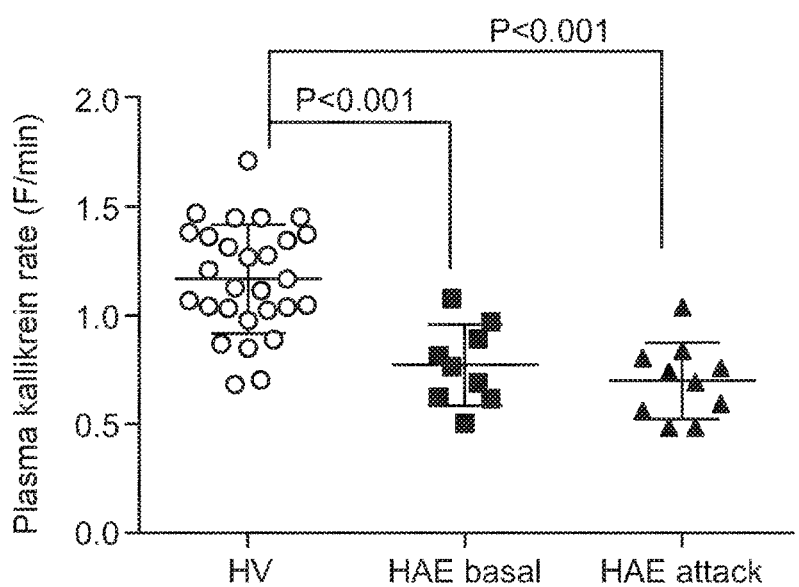
FIG. 2 presents a plot showing the rate of plasma kallikrein generation following activation with FXIIa in plasma samples from patients having HAE (type I/type II) at basal level ("HAE basal," N=9), from HAE patients during an HAE attack ("HAE attack," N=10), and from healthy individuals ("HV," N+28).

Plasma samples from HAE patients and healthy individuals were also evaluated for plasma kallikrein generation. Briefly, citrated plasma samples were activated with FXIIa, followed by FXIIa quenching with corn trypsin inhibitor. There was a slight decrease in the rate of plasma kallikrein in samples from HAE patients relative to normal levels (FIG. 2).

Figure 3:
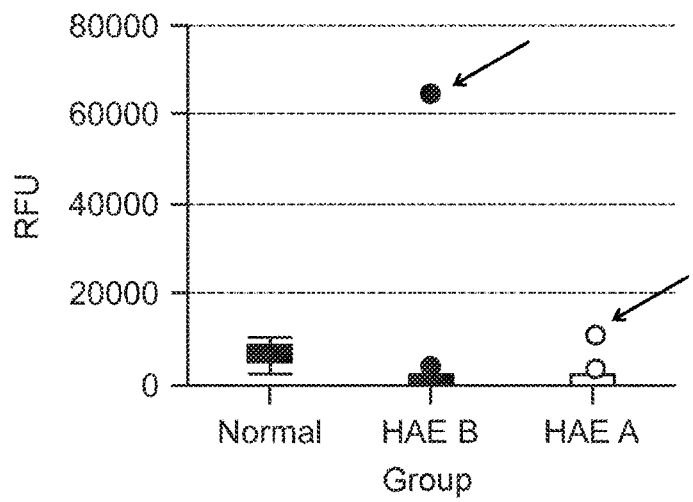
FIG. 3 presents box plots showing C1-esterase inhibitor (C1-INH) protein levels detected in plasma samples from patients having HAE (type I/type II) at basal level ("HAE B," N=18) and during an HAE attack ("HAE A," N=19) and healthy individuals ("Normal," N=22). A: shows C1-INH detected in plasma samples from each individual, including an outlier indicated with an arrow. B: shows C1-INH detected in plasma samples from each individual, with the outlier omitted. RFU is relative fluorescence units. The mean C1-INH in plasma samples from healthy patients is 6522 RFU±1852 (standard deviation, SD). The mean C1-INH in plasma samples from patients having HAE at basal level is 1231 RFU±673 (SD), and the mean C1-INH in plasma samples from patients having HAE during an is 1082 RFU±530 (SD).
Figure 3:
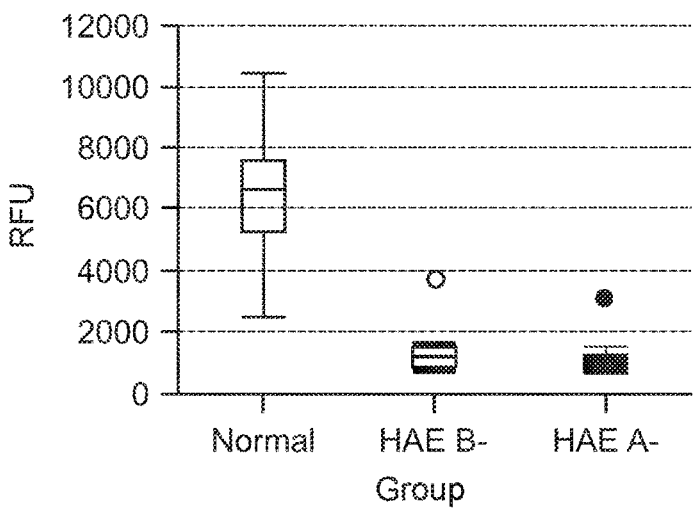

In this study, 15 of the 33 subjects with HAE were being treated prophylactically with a C1-INH, CINRYZE®, which would increase the amount of plasma C1-INH detected. However, in HAE patients not being treated prophylactically with C1-INH, total C1-INH was decreased as compared to normal plasma samples (FIG. 3, panel A). As indicated in FIG. 3, panel A with an arrow, plasma samples from one subject contained elevated levels of C1-INH basal and attack conditions. When this outlier sample was omitted, the data showed a clear reduction in plasma C1-INH in HAE patients (FIG. 3, panel B).

Figure 4:
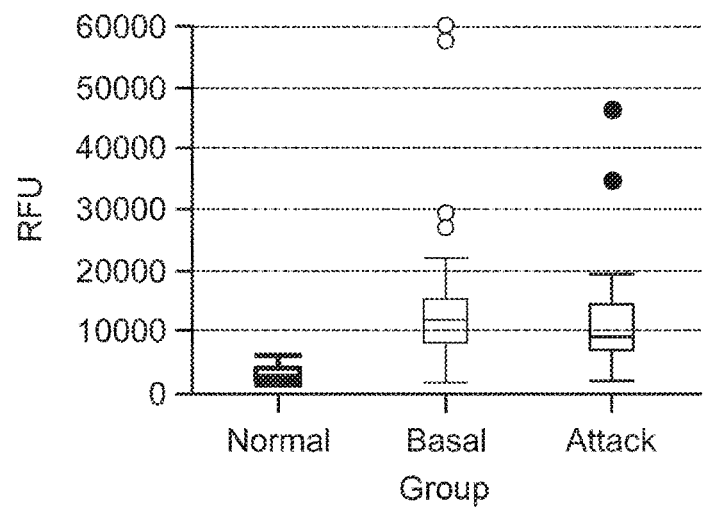
FIG. 4 presents box plots showing levels of several proteins involved in mitochondrial function detected in plasma samples from patients having HAE (type I/type II) at basal level ("HAE B") and during an HAE attack ("HAE A") and healthy individuals ("Normal"). A: ATP synthase subunit O levels. B: cyclophilin F levels. C: mitochondrial heat shock protein 60 (HSP60). RFU is relative fluorescence units.
Figure 4:
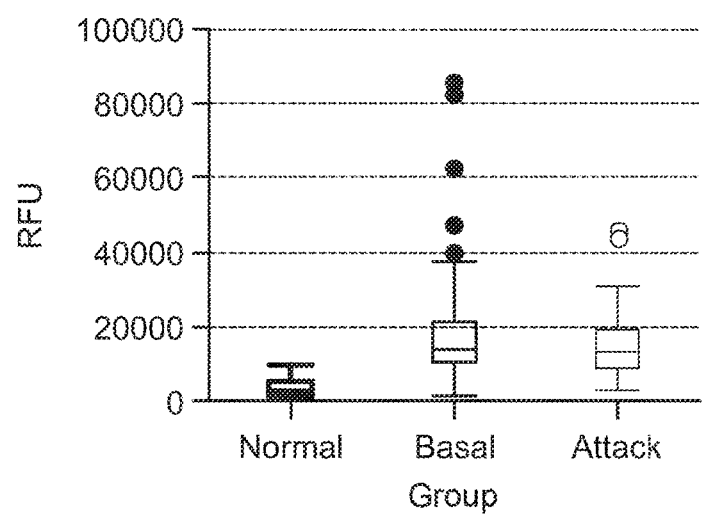

The proteomic data also provided novel insight into the pathobiology of HAE. For example, a subset of the proteins identified as being elevated in plasma samples from HAE patients are associated with mitochondrial function (FIG. 4, panels A-C). ATP synthase subunit O (ATPO) is an essential mitochondrial membrane protein (also known as $F_1F_0$ ATP synthase or Complex V) that produces ATP from ADP in the presence of a proton gradient across the mitochondrial membrane, which is generated by electron transport complexes of the respiratory chain. Similarly, cyclophillin F (also known as cyclophillin D or peptidyl-prolyl cis-trans isomerase F, mitochondrial, EC: 5.2.1.8) is also a mitochondrial membrane protein. Levels of the 60 kDa mitochondrial heat shock protein (HSP60) were also found to be elevated in plasma samples from HAE patients.

Figure 5:
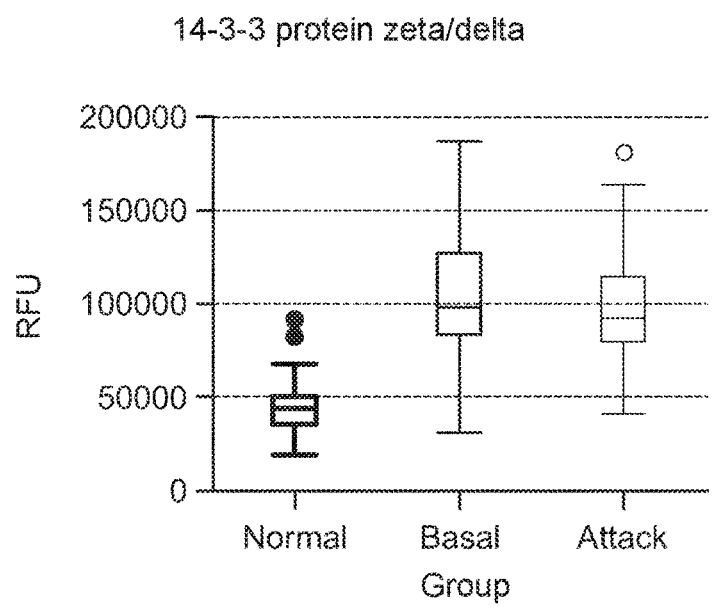
FIG. 5 presents a box plot showing 4-3-3 protein zeta/delta protein levels detected in plasma samples from patients having HAE (type I/type II) at basal level ("HAE B," N=33) and during an HAE attack ("HAE A," N=33) and healthy individuals ("Normal," N=22). RFU is relative fluorescence units.

An additional protein identified in the proteomic analysis that may be used as a biomarker for HAE is 14-3-3 zeta/delta (14-3-3ζ) protein. As shown in FIG. 5, the level of the 14-3-3 zeta/delta protein was elevated in plasma from HAE patients as compared to healthy individuals. The 14-3-3 zeta/delta protein is one of a 7 member protein family, of which other members were also found to be elevated in plasma from HAE patients, including 14-3-3 beta/alpha (Table 1). The 14-3-3 proteins are ubiquitously expressed and highly conserved among plants and mammals and are involved in the regulation of signal transduction pathways involved in metabolism, transcription, apoptosis, protein transport, and cell cycle regulation (Aghazadeh et al. *Drug Discov. Today* (2015)). Altered plasma or serum levels of these proteins have been associated with the occurrence of diseases such as rheumatoid arthritis (Maksymowych et al. *Clin. Exp. Rheumatol.* (2014) 32: S35-S39), large vessel vasculitis including Takayasu arteritis and giant cell arteritis (Chakravarti et al. *Arthritis Rheumatol.* (2015) 67: 1913-1921), cancer (Matta et al. *Exper Opin. Ther. Targets* (2012) 16: 515-523), Parkinson's disease (Slone et al. *Neurobiol. Dis.* (2015) 79: 1-13), and Alzheimer's disease (Steinacker et al. *Semin. Cell Dev. Biol.* (2011) 22: 696-704). The results described herein are the first identification of elevated 14-3-3 zeta/delta protein levels in plasma from HAE patients as compared to plasma from healthy volunteers.

Figure 6:
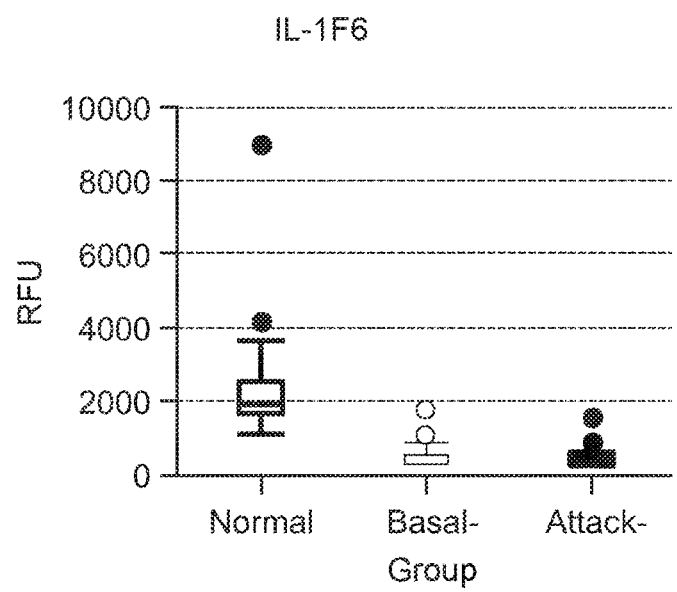
FIG. 6 presents a box plot showing IL-1F6 protein levels in plasma samples from patients having HAE (type I/type II) at basal level ("HAE B," N=33) and during an HAE attack ("HAE A," N=33) and healthy individuals ("Normal," N=22). RFU is relative fluorescence units.
Figure 7:
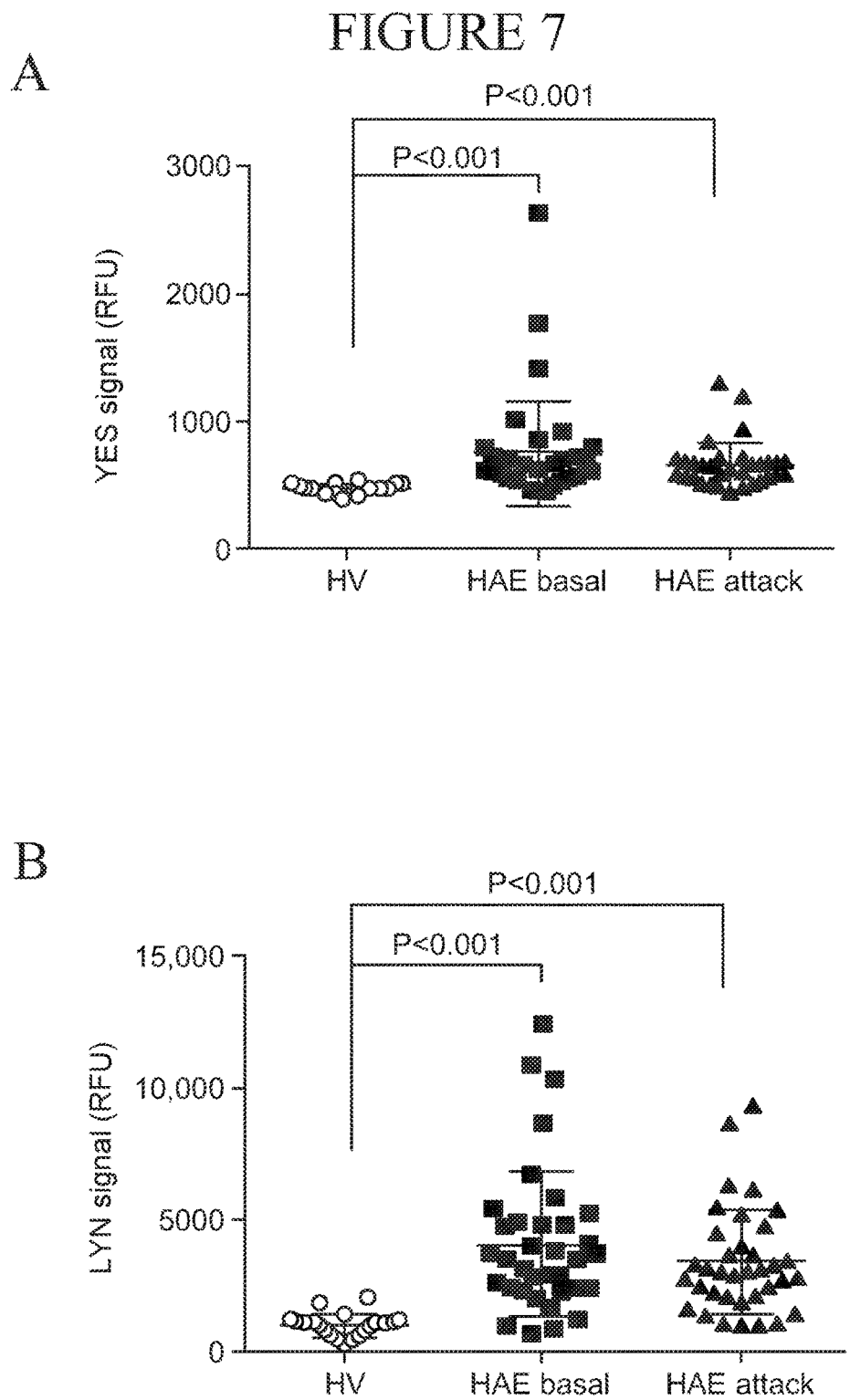
FIG. 7 presents a graph showing protein kinase levels in plasma samples from patients having HAE (type I/type II) at basal level ("HAE basal"), from HAE patients during an HAE attack ("HAE attack") and from healthy individuals ("HV"). A: tyrosine-protein kinase (YES). B: tyrosine-protein kinase Lyn (LYN). C: mitogen-activated protein kinase 14 (MAPK14). RFU is relative fluorescence units.
Figure 9:
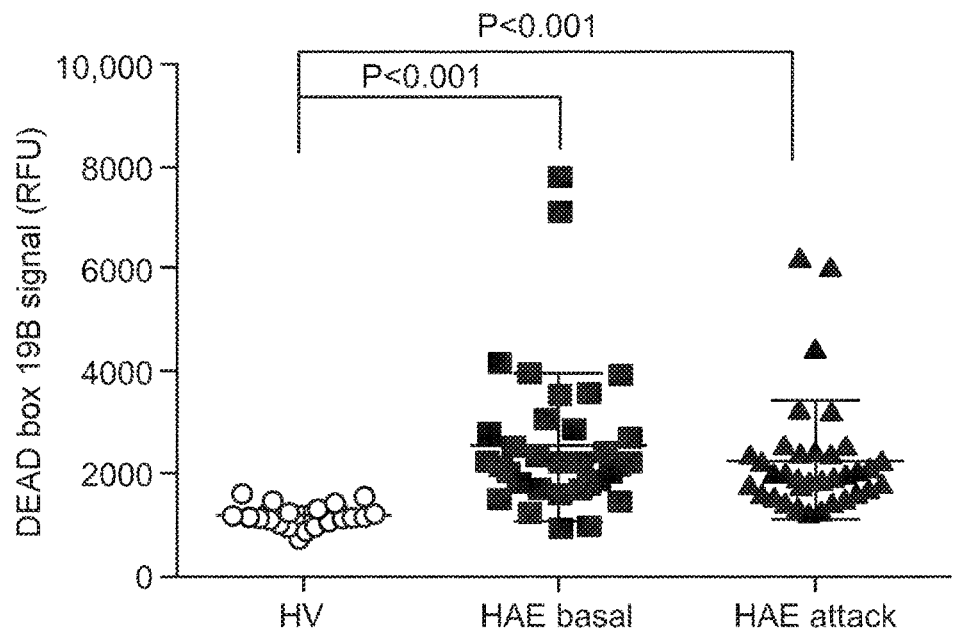
FIG. 9 presents a graph showing ATP-dependent RNA helicase DDX19B (DEAD box protein 19B) protein levels in plasma samples from patients having HAE (type I/type II) at basal level ("HAE basal"), from HAE patients during an HAE attack ("HAE attack), and from healthy individuals ("HV"). RFU is relative fluorescence units.
Figure 10:
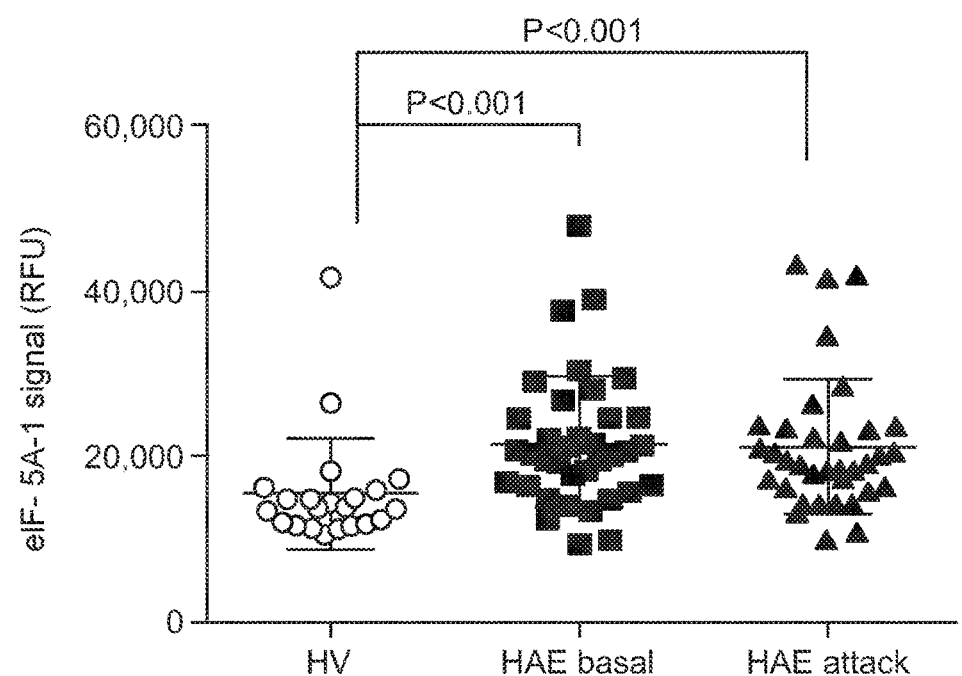
FIG. 10 presents a graph showing eukaryotic translation initiation factor 5A 1 (eIF-5A-1) protein levels in plasma samples from patients having HAE (type I/type II) at basal level ("HAE basal"), from HAE patients during an HAE attack ("HAE attack), and from healthy individuals ("HV"). RFU is relative fluorescence units.

Additional proteins identified as deviating in plasma from patients having HAE as compared to healthy individuals include IL-1F6 (also known as interleukin-36 alpha); protein kinases: tyrosine protein kinase YES, tyrosine protein kinase LYN, and mitogen-activated protein kinase 14 (MAPK14); glycogen synthase kinase 3 alpha/beta (GSK 3 alpha/beta); ATP-dependent RNA helicase DDX19B (DEAD box protein 19B); and eukaryotic translation initiation factor 5A 1 (eIF-5A-1) (Table 1). As shown in FIG. 6, levels of IL-1F6 were significantly lower in plasma samples from HAE patients; whereas as shown in FIGS. 7-10, each of tyrosine protein kinase YES, tyrosine protein kinase LYN, MAPK14, GSK 3 alpha/beta, DEAD box protein 19B, and eIF-5A-1 were significantly elevated in plasma samples from HAE patients.

The proteomic analysis identified over 150 proteins that were present at levels that differed between patients with HAE and healthy individuals. Any of the proteins identified herein, may be used as a biomarker (individually or in combination (biomarker set)) for diseases associated with the contact activation system, for example in methods for identifying patients who are at risk of a disease associated with the contact activation system (e.g., HAE), selecting a candidate for treatment, monitoring disease progression or disease state, assessing the efficacy of a treatment against a disease, determining a course of treatment, identifying whether a disease or disorder is associated with the contact activation system, and/or for research purposes, including, e.g., studying the mechanism of a disease, which may be relied upon for the development of new therapies.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method, comprising:
   (i) providing a biological sample obtained from a subject having or suspected of having hereditary angioedema (HAE); and
   (ii) measuring the level of a protein biomarker set, which comprises Interleukin-36 alpha (IL-1F6);
   (iii) identifying the subject as a patient having HAE if the level of IL-1F6 in the biological sample obtained from the subject is at least 1.1-fold lower than the level of IL-1F6 of a control subject, wherein the control subject is a subject not having HAE; and
   (iv) administering to the subject identified as having HAE an effective amount of a therapeutic agent for treating HAE; wherein therapeutic agent is a plasma kallikrein (pKal) inhibitor, a bradykinin 2 receptor (B2R) inhibitor, and/or a C1 esterase inhibitor.

2. The method of claim 1, wherein the protein biomarker set consists of 2-10 proteins.

3. The method of claim 1, wherein the biological sample is a serum sample or a plasma sample.

4. The method of claim 1, wherein the HAE is type I HAE or type II HAE.

5. The method of claim 1, wherein step (i) comprises collecting the biological sample into an evacuated blood collection tube, which comprises one or more protease inhibitors.

6. The method of claim 1, wherein step (ii) is performed using an enzyme-linked immunosorbent assay (ELISA), an immunoblotting assay, or a lateral flow assay.

7. The method of claim 1, wherein the subject is a human patient.

8. The method of claim 1, wherein the pKal inhibitor is an anti-pKal antibody or an inhibitory peptide.

9. The method of claim 8, wherein the pKal inhibitor is lanadelumab or ecallantide.

10. The method of claim 1, wherein the B2R inhibitor is an inhibitory peptide, optionally wherein the inhibitory peptide is icatibant.

11. The method of claim 1, wherein the therapeutic agent is a C1 esterase inhibitor, which is a human plasma-derived C1 esterase inhibitor.

12. The method of claim 1, wherein the protein biomarker set further comprises
   a mitochondrial protein selected from the group consisting of ATP synthase subunit 0 (ATPO), cyclophilin F, and mitochondrial heat shock protein 60 (HSP60).

13. The method of claim 1, wherein the protein biomarker set further comprises 14-3-3 zeta/delta or 14-3-3 beta/alpha.

14. The method of claim 1, wherein the protein biomarker set further comprises a protein kinase selected from the group consisting of protein kinase YES, protein kinase LYN, and mitogen-activated protein kinase 14 (MAPK14).

15. The method of claim 1, wherein the protein biomarker set further comprises a protein selected from the group consisting of glycogen synthase kinase 3 alpha/beta, ATP-dependent RNA helicase DDX19B, and eukaryotic translation initiation factor 5A-1.

16. The method of claim 1, wherein the level of IL-1F6 in the biological sample obtained from the subject is at least 1.5-fold lower than the level of IL-1F6 of the control subject.

17. The method of claim 1, wherein the level of IL-1F6 in the biological sample obtained from the subject is at least 2.0-fold lower than the level of IL-1F6 of the control subject.

18. The method of claim 1, wherein the level of IL-1F6 in the biological sample obtained from the subject is at least 5-fold lower than the level of IL-1F6 of the control subject.

* * * * *